United States Patent
Green et al.

(10) Patent No.: US 10,550,440 B2
(45) Date of Patent: Feb. 4, 2020

(54) SYNTHETIC TRANSLATION-SENSING RIBOSWITCHES AND USES THEREOF

(71) Applicant: ARIZONA BOARD OF REGENTS ON BEHALF OF ARIZONA STATE UNIVERSITY, Scottsdale, AZ (US)

(72) Inventors: Alexander A. Green, Scottsdale, AZ (US); Anli Tang, Gilbert, AZ (US)

(73) Assignee: ARIZONA BOARD OF REGENTS ON BEHALF OF ARIZONA STATE UNIVERSITY, Scottsdale, AZ (US)

(*) Notice: Subject to any disclaimer, the term of this patent is extended or adjusted under 35 U.S.C. 154(b) by 0 days.

(21) Appl. No.: 16/079,740

(22) PCT Filed: Feb. 27, 2017

(86) PCT No.: PCT/US2017/019687
§ 371 (c)(1),
(2) Date: Aug. 24, 2018

(87) PCT Pub. No.: WO2017/147585
PCT Pub. Date: Aug. 31, 2017

(65) Prior Publication Data
US 2019/0071737 A1 Mar. 7, 2019

Related U.S. Application Data

(60) Provisional application No. 62/300,276, filed on Feb. 26, 2016.

(51) Int. Cl.
| | |
|---|---|
| *C12Q 1/6897* | (2018.01) |
| *C12N 15/113* | (2010.01) |
| *C12N 15/67* | (2006.01) |
| *C07K 14/435* | (2006.01) |

(52) U.S. Cl.
CPC ...... *C12Q 1/6897* (2013.01); *C07K 14/43595* (2013.01); *C12N 15/113* (2013.01); *C12N 15/67* (2013.01); *C07K 2319/60* (2013.01)

(58) Field of Classification Search
None
See application file for complete search history.

(56) References Cited

U.S. PATENT DOCUMENTS

| | | |
|---|---|---|
| 5,162,209 A | 11/1992 | Scheele |
| 5,468,613 A | 11/1995 | Erlich et al. |
| 5,512,462 A | 4/1996 | Cheng |
| 5,580,726 A | 12/1996 | Villeponteau et al. |
| 5,599,672 A | 2/1997 | Liang et al. |
| 2005/0153282 A1 | 7/2005 | Linnen et al. |
| 2013/0143955 A1 | 6/2013 | Breaker et al. |
| 2015/0275203 A1 | 10/2015 | Green et al. |
| 2016/0153036 A1 | 6/2016 | Chen et al. |

FOREIGN PATENT DOCUMENTS

| | | |
|---|---|---|
| EP | 0328829 B1 | 9/1995 |
| WO | 1995021944 A1 | 8/1995 |
| WO | 2004046321 A2 | 6/2004 |
| WO | 2012058488 A1 | 5/2012 |
| WO | 2014074648 A2 | 5/2014 |
| WO | 2016011089 A1 | 1/2016 |
| WO | 2017087530 A1 | 5/2017 |
| WO | 2018026762 A1 | 2/2018 |
| WO | 2018027177 A1 | 2/2018 |
| WO | 2018075502 A1 | 4/2018 |

OTHER PUBLICATIONS

Chalifour, L. et al., "A Method for Analysis of Gene Expression Patterns", Analytical Biochemistry, Feb. 1994 [retrieved on Dec. 17, 2018], 216(2), pp. 299-304, retrieved from the internet <URL: https://www.sciencedirect.com/science/article/pii/S0003269784710451> <https://doi.org/10.1006/abio.1994.1045>.

Feng, C. et al., "Hairpin assembly circuit-based fluorescence cooperative amplification strategy for enzyme-free and label-free detection of small molecule", Talanta, Oct. 2015 [available online May 2015, retrieved on Dec. 17, 2018], 143, pp. 101-106, retrieved from the internet <URL: https://www.sciencedirect.com/science/article/pii/S0039914015300230?via%3Dihub> <https://doi.org/10.1016/j.talanta.2015.05.072>.

Gibson, D. et al., "Enzymatic assembly of DNA molecules up to several hundred kilobases", Nature Methods, May 2009 [available online Apr. 2009, retrieved on Dec. 17, 2018], 6(5), pp. 343-345, retrieved from the internet <URL: https://www.nature.com/articles/nmeth.1318> <https://doi.org/10.1038/nmeth.1318>.

Green, A. et al., "Complex cellular logic computation using ribocomputing devices", Nature, Aug. 2017 [available online Jul. 2017, retrieved on Dec. 17, 2018], 548, pp. 117-121, retrieved from the internet <URL: https://www.nature.com/articles/nature23271> <https://doi.org/10.1038/nature23271>.

Green, A. et al., "Toehold switches: de-novo-designed regulators of gene expression", Cell, Nov. 2014 [available online Oct. 2014, retrieved on Dec. 17, 2018], 159(4), pp. 925-939, retrieved from the internet <URL: https://www.sciencedirect.com/science/article/pii/S0092867414012896?via%3Dihub> <https://doi.org/10.1016/j.cell.2014.10.002>.

(Continued)

*Primary Examiner* — Channing S Mahatan
(74) *Attorney, Agent, or Firm* — Quarles & Brady LLP; Jessica L. Lewis

(57) ABSTRACT

Provided herein is a RNA-based riboregulator that detects protein translation and uses this stimulus to regulate expression of an unrelated protein. In one embodiment, provided herein is a synthetic nucleic acid molecule configured as a translation-sensing riboregulator, where the synthetic nucleic acid molecule comprises a first nucleotide sequence encoding a polypeptide, a translation-sensing riboswitch (TSR), and a second nucleotide sequence encoding a polypeptide, wherein the translation-sensing riboswitch comprises a stop codon of the first nucleotide sequence, a fully or partially double-stranded stem-forming domain, and translation initiation elements of the second nucleotide sequence.

12 Claims, 8 Drawing Sheets

Specification includes a Sequence Listing.

(56) References Cited

OTHER PUBLICATIONS

Moon, T. et al., "Production of Glucaric Acid from a Synthetic Pathway in Recombinant *Escherichia coli*", Applied and Environmental Microbiology, Feb. 2009 [available online Jan. 2009, retrieved on Dec. 17, 2018], 75(3), pp. 589-595, retrieved from the internet <URL: https://aem.asm.org/content/75/3/589> <DOI: 10.1128/AEM.00973-08>.

Moon, T. et al., Correction to "Production of Glucaric Acid from a Synthetic Pathway in Recombinant *Escherichia coli*", Applied and Environmental Microbiology, Jul. 2009 [available online Jun. 2009, retrieved on Dec. 17, 2018], 75(13), p. 4660, retrieved from the internet <URL: https://aem.asm.org/content/75/13/4660> <DOI: 10.1128/AEM.01065-09>.

Nguyen, C. et al., "Differential gene expression in the murine thymus assayed by quantitative hybridization of arrayed cDNA clones", Genomics, Sep. 1995 [retrieved on Dec. 17, 2018], 29(1), pp. 207-216, retrieved from the internet <URL: https://www.sciencedirect.com/science/article/pii/S0888754385712335?via%3Dihub> <https://doi.org/10.1006/geno.1995.1233>.

Oppenheim, D. et al., "Translational coupling during expression of the tryptophan operon of *Escherichia coli*", Genetics, Aug. 1980 [retrieved on Dec. 17, 2018], 95(4), pp. 785-795, retrieved from the internet <URL: http://www.genetics.org/content/genetics/95/4/785.full.pdf>.

Pardee, K. et al., "Rapid, Low-Cost Detection of Zika Virus Using Programmable Biomolecular Components", Cell, May 2016 [retrieved on Dec. 17, 2018], 165(5), pp. 1255-1266, retrieved from the internet <URL: https://www.sciencedirect.com/science/article/pii/S0092867416305050?via%3Dihub> <https://doi.org/10.1016/j.cell.2016.04.059>.

Patent Cooperation Treaty, International Searching Authority, Search Report for PCT/US2017/044810, 4 pages, report dated Oct. 20, 2017.

Patent Cooperation Treaty, International Searching Authority, Search Report for PCT/US2017/045585, 3 pages, report dated Oct. 25, 2017.

Patent Cooperation Treaty, International Searching Authority, Search Report for PCT/US2017/056960, 5 pages, report dated Feb. 22, 2018.

Patent Cooperation Treaty, International Searching Authority, Written Opinion for PCT/US2017/044810, 7 pages, report dated Oct. 20, 2017.

Patent Cooperation Treaty, International Searching Authority, Written Opinion for PCT/US2017/045585, 8 pages, report dated Oct. 25, 2017.

Patent Cooperation Treaty, International Searching Authority, Written Opinion for PCT/US2017/056960, 7 pages, report dated Feb. 22, 2018.

Pietu, G. et al., "Novel gene transcripts preferentially expressed in human muscles revealed by quantitative hybridization of a high density cDNA array", Genome Research, Jun. 1996 [retrieved on Dec. 17, 2018], 6(6), pp. 492-503, retrieved from the internet <URL: https://genome.cshlp.org/content/6/6/492.full.pdf+html> <doi:10.1101/gr.6.6.492>.

Rex, G. et al., "The mechanism of translational coupling in *Escherichia coli*. Higher order structure in the atpHA mRNA acts as a conformational switch regulating the access of de novo initiating ribosomes", Journal of Biological Chemistry, Jul. 1994 [retrieved on Dec. 17, 2018], 269(27), pp. 18118-18127, retrieved from the internet <URL: http://www.jbc.org/content/269/27/18118.long>.

Tang, A. et al., "Synthetic Translation-Sensing Riboswitches", Poster, presented on Feb. 27, 2016, ASU Memorial Union (Ventana Room 241).

Tian, T. et al., "A predictive biophysical model of translational coupling to coordinate and control protein expression in bacterial operons", Nucleic Acids Research, Aug. 2015 [available online Jun. 2015, retrieved on Dec. 17, 2018], 43(14), pp. 7137-7151, retrieved from the internet <URL: https://www.ncbi.nlm.nih.gov/pmc/articles/PMC4538824/> <doi:10.1093/nar/gkv635>.

Zadeh, J. et al., "NUPACK: Analysis and design of nucleic acid systems", Journal of Computation Chemistry, Jan. 2011 [available online Nov. 2010, retrieved on Dec. 17, 2018], 32(1), pp. 170-173, retrieved from the internet <URS: https://onlinelibrary.wiley.com/doi/full/10.1002/jcc.21596> <https://doi.org/10.1002/jcc.21596 >.

Zhao, N. et al., "High-density cDNA filter analysis: a novel approach for large-scale, quantitative analysis of gene expression", Gene [retrieved on Dec. 17, 2018], Apr. 1995, 156(2), pp. 207-213, retrieved from the internet <https://www.sciencedirect.com/science/article/pii/037811199500023Y?via%3Dihub> <https://doi.org/10.1016/0378-1119(95)00023-Y>.

International Search Report and Written Opinion for International Patent Application No. PCT/US2017/0196687 dated May 5, 2017.

Caron, MP et al., Dual-Acting Riboswitch Control of Translation Initiation and mRNA Decay. PNAS. Nov. 19, 2012; vol. 109, No. 50; pp. 444-453, supplementary; figures 1A, 3A; supplementary p. 2, paragraph 2; supplementary p. 7, paragraph 1; figure S2; DOI: 10.1073/pnas.1214024109.

Green, AA et al., Toehold Switches: De-Novo-Designed Regulators of Gene Expression. Cell. Oct. 23, 2014; vol. 159, No. 4; pp. 925-939, S1-S8; p. 928, col. 1, paragraph 3; p. 928, col. 2, paragraph 3; p. 931, column 1, paragraph 4—col. 2, paragraph 2; figures 4A-4E; DOI: 10.1016/j.cell.2014.10.002.

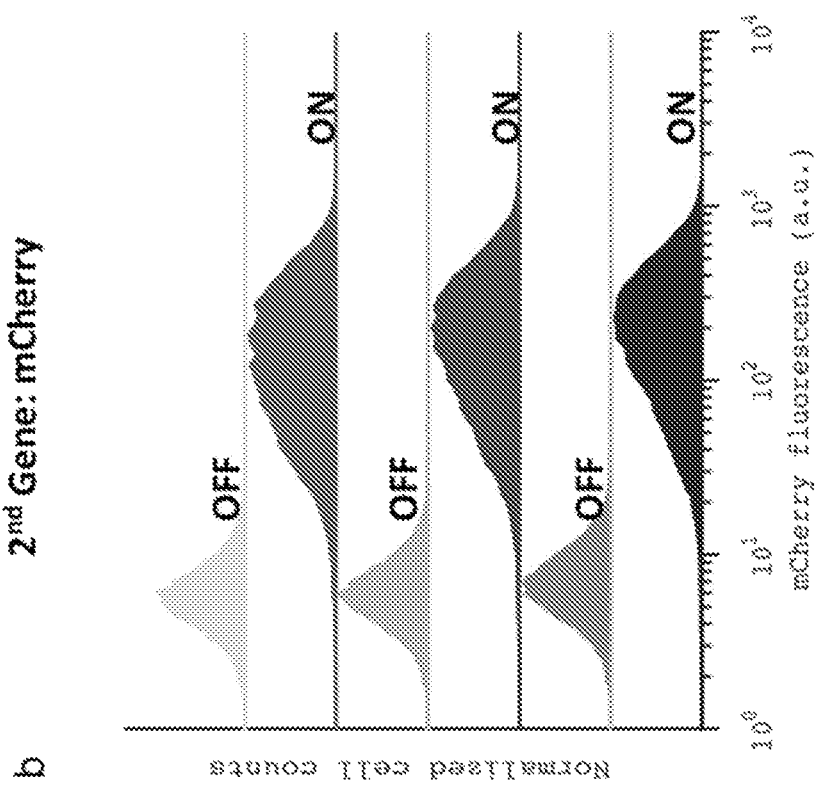
FIGS. 2A-2C, CONTINUED

FIGS. 2A-2C, CONTINUED
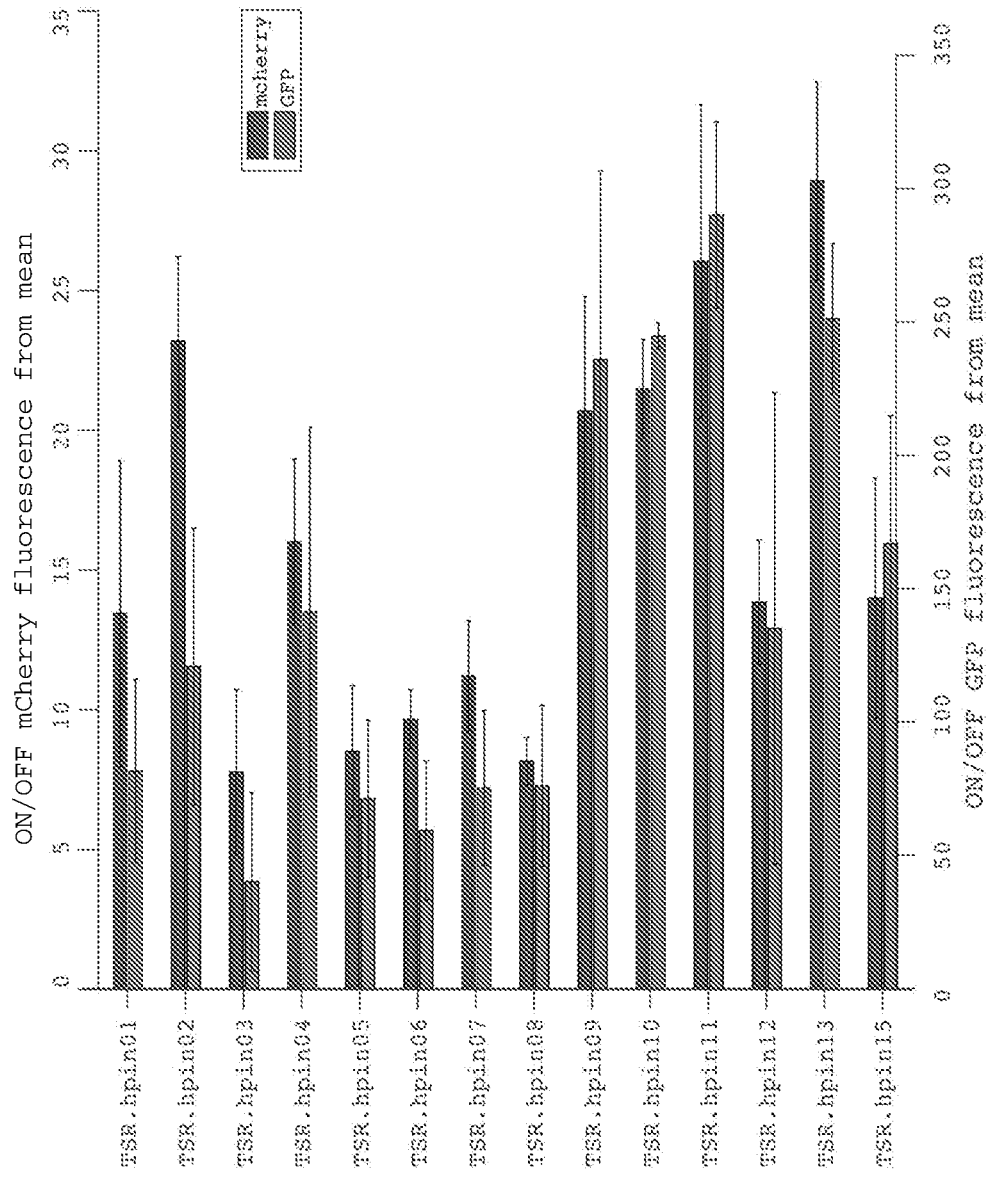
C.

FIGS. 4A-4C, CONTINUED
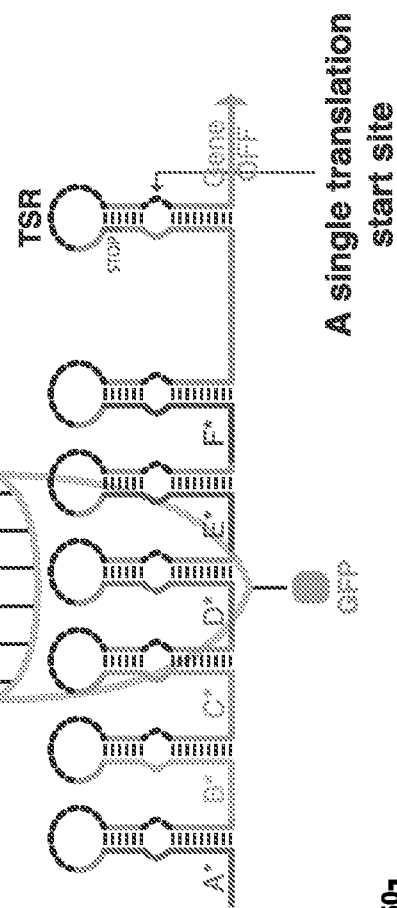
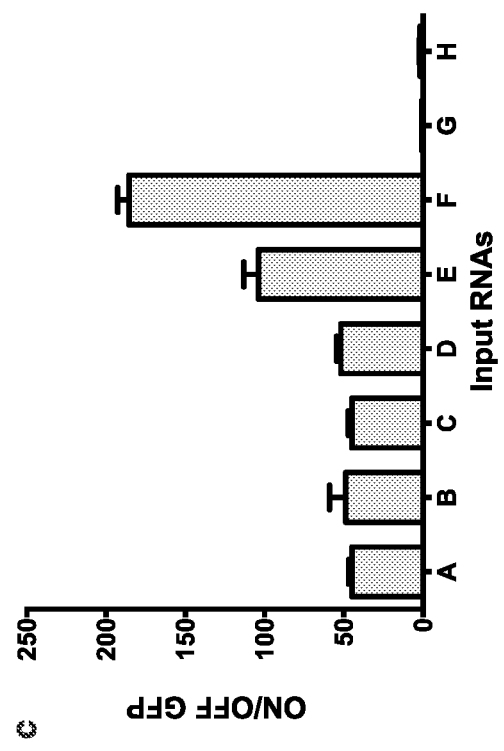

SYNTHETIC TRANSLATION-SENSING RIBOSWITCHES AND USES THEREOF

CROSS-REFERENCE TO RELATED APPLICATIONS

This application represents the national stage entry of PCT International Application No. PCT/US2017/019687, filed on Feb. 27, 2017, and claims priority to U.S. Provisional Application No. 62/300,276, filed Feb. 26, 2016, which is incorporated by reference herein as if set forth in its entirety.

BACKGROUND

Bacteria commonly express enzymes in metabolic pathways using polycistronic mRNAs that encode the sequences of multiple genes. Translation of these genes is governed by a phenomenon known as translational coupling, which ties the expression levels of downstream genes within the mRNA to those located upstream. The atp operon in *E. coli*, for instance, provides a well-known example of translational coupling. In this operon, translation of the downstream gene (atpA) is normally blocked by a hairpin secondary structure at the end of the upstream gene (atpH). The inhibitory mRNA hairpin only opens to allow translation of atpA when the upstream atpH is being translated.

Despite their widespread use in nature, it has been difficult to rationally engineer the translational coupling between genes on the same polycistronic transcript and efforts to engineer synthetic translational couplers remain in their infancy. The translational efficiency of the downstream gene is strongly dependent on the secondary structure of the ribosomal binding site (RBS) and start codon, yet these features change with each modification to nearby sequences at the end of the upstream gene. Moreover, translational coupling is tied to the procession of the ribosome along the mRNA, a dynamic ribonucleoprotein interaction that is far harder to model than RNA secondary structures alone. Accordingly, there remains a need in the art for a synthetic RNA-based mechanism for detecting translation and modulating expression of a downstream gene without the need for any changes to the output protein sequence.

SUMMARY

In one aspect, provided herein is a synthetic nucleic acid molecule comprising a first nucleotide sequence encoding a first polypeptide, a translation-sensing riboswitch (TSR), and a second nucleotide sequence encoding a second polypeptide. The translation-sensing riboswitch can comprise a stop codon of the first nucleotide sequence, a fully or partially double-stranded stem-forming domain, and translation initiation elements of the second nucleotide sequence. The TSR can be configured to adopt a translationally active ON state when the first polypeptide is being translated. One or both of the first and second nucleotide sequences can encode a fluorescent polypeptide. The fluorescent polypeptide can be Green Fluorescent Protein (GFP) or mCherry. The synthetic nucleic acid can further comprise a toehold switch located upstream of the first nucleotide sequence, wherein the toehold switch comprises a fully or partially double-stranded stem-forming domain, a loop-forming domain comprising a ribosomal binding site (RBS), and a trigger recognition sequence.

In another aspect, provided herein is a synthetic nucleic acid molecule comprising a first nucleotide sequence encoding a first polypeptide, a translation-sensing riboswitch inverter (TSRi), and a second nucleotide sequence encoding a second polypeptide. The TSRi can comprise a stop codon of the first nucleotide sequence, a fully or partially double-stranded stem-forming domain, and translation initiation elements of the second nucleotide sequence, and wherein the TSRi is configured to adopt a translationally inactive OFF state when the first polypeptide is being translated. One or both of the first and second polypeptides can be a fluorescent polypeptide. The fluorescent polypeptide can be Green Fluorescent Protein (GFP) or mCherry.

In a further aspect, provided herein is a method for detecting response of a cell to a stimulus. The method comprises introducing into a cell a synthetic nucleic acid molecule comprising a first nucleotide sequence encoding a first polypeptide, a translation-sensing riboswitch (TSR), and a second nucleotide sequence encoding a second polypeptide, wherein the translation-sensing riboswitch comprises a stop codon of the first nucleotide sequence, a fully or partially double-stranded stem-forming domain, and translation initiation elements of the second nucleotide sequence; detecting an expression level of each of the first and second polypeptides in the cell; exposing the cell comprising the introduced molecule to a stimulus; and detecting an expression level of each of the first and second polypeptides in the exposed cell, wherein an increase in expression of the second polypeptide following exposure relative to its expression prior to exposure indicates that translation of the first polypeptide was upregulated in the presence of the stimulus, and wherein a decrease in expression of the second polypeptide following exposure relative to its expression prior to exposure indicates that translation of the first polypeptide was downregulated in the presence of the stimulus. The first polypeptide can be endogenous to the cell. The second polypeptide can be a fluorescent polypeptide. The fluorescent polypeptide can be Green Fluorescent Protein (GFP) or mCherry. The stimulus can be a chemical compound.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein.

Figure 1A:
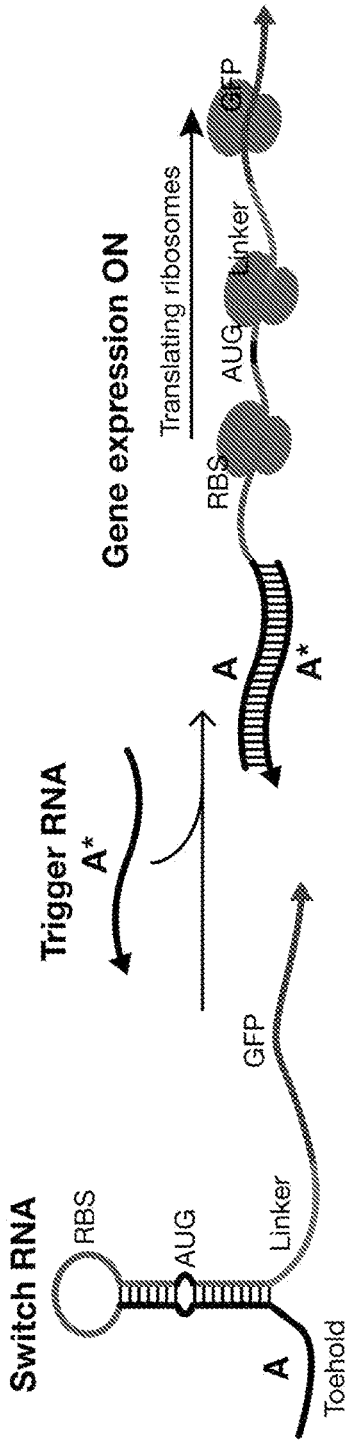
FIGS. 1A-1B present design schematics of the toehold switch and the synthetic translation-sensing riboswitch (TSR). (A) The toehold switch employs a hairpin structure containing an in-loop ribosomal binding site (RBS) and start codon (AUG) concealed within the stem to strongly repress expression of a gene, such as green fluorescent protein (GFP). A 5' single-stranded region called a toehold is used to initiate a hybridization reaction with a trigger RNA with the complementary sequence A* to the A sequence in the switch RNA. Binding of the trigger RNA disrupts the switch RNA stem and exposes the RBS and start codon. The newly freed RBS and start codon can then enable translation of the downstream gene. (B) The TSRs adopt the same hairpin secondary structure used by toehold switches with an in-loop RBS. The TSR hairpin contains the stop codon of the upstream input gene (GFP in this case) and the start codon of the downstream output gene (mCherry in this case). For testing purposes, a toehold switch hairpin is used to regulate the input GFP. When a trigger RNA is not present, input GFP is not translated and the TSR hairpin remains intact, preventing translation of output mCherry. When the system is supplied with a cognate trigger for the toehold switch, the first RBS is exposed and translation of the input gene begins as the ribosome travels down the transcript. Finally, the progress of the ribosome unwinds the TSR hairpin, exposes the second RBS, and activates expression of the output mCherry.

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though each patent publication, patent, and patent application is set forth in its entirety in the present application.

The methods provided herein are based at least in part on the inventors' discovery of a new class of translational couplers known as "translation-sensing riboswitches" or TSRs designed to detect translational coupling and regulate expression of an unrelated protein based on the detected translation. As used herein, the term "translational coupler" refers to a synthetic means for regulating transcription in which translation of one protein influences another. The translation-sensing riboswitches provided herein enable expression of multiple genes that are coupled, meaning located on same polycistronic transcript. This disclosure, therefore, provides a variety of translation-sensing riboswitches and "devices" derived therefrom that offer a non-leaky and robust form of post-transcriptional regulation that has not previously been exploited for rational genetic engineering. Advantages of the synthetic translation-sensing riboswitches provided herein are multifold and include, for example, the activation or deactivation of multiple genes (e.g., multiple genes on the same polycistronic transcript) in response to single post-transcriptional activation event, as well as RNA-based regulation without requiring any changes to an output protein sequence.

Previous attempts to generate synthetic translational couplers in *E. coli* (Tian & Salis, 2015, *Nucleic Acids Res* 43(14):7137-7151) have required substantial modifications to the sequences of both the upstream and downstream genes, which could affect their folding and function when expressed. These sequence modifications are required to introduce two hairpins of high secondary structure to the upstream and downstream genes, leading to couplers that are ~70 nucleotides in length. In addition, the Tian and Salis systems can display leakage in the expression of the downstream gene. By contrast, the synthetic translation-sensing RNA devices provided herein do not require any changes to the output protein sequence to regulate expression of the downstream gene, provide negligible downstream gene leakage, and are genetically compact at a length of 48 nucleotides, which could be as short as 25 nucleotides. These devices are thus ideally suited for use in applications such as metabolic engineering, in vivo logic systems, in vitro diagnostics, and direct monitoring of translation in vivo. The inventors addressed limitations associated with translational coupling using an interaction mechanism based on RNA-based hairpin structures and strategic placement of ribosome binding sites (RBS) and start and stop codons. As described in the paragraphs that follow and the Example, the inventors engineered multiple constructs comprising hairpin structures, varying the position of the stop codon relative to the start codon, which exhibited low leakage and average ON/OFF ratios exceeding 15. Without being bound by any particular theory or mechanism of action, it is believed that, by inserting one or more TSRs upstream of a gene of interest or integrating them into more complex genetic circuits, the riboregulators provided herein allows the activation of multiple genes in response to single post-transcriptional activation event and enable RNA-based regulation without necessitating any changes to the output protein sequence.

Accordingly, in a first aspect, provided herein is a synthetic translation-sensing riboswitch or TSR. As used herein, the term "translation-sensing riboswitch" (TSR) refers to a synthetic RNA construct comprising structural elements that activate or deactivate expression of one or more genes in response to the presence or absence of a triggering stimulus, namely upstream protein translation. The base design of the synthetic translation-sensing RNA devices described herein was inspired by the toehold switch (Green et al., 2014, *Cell* 159:925-939), which is a recently developed synthetic riboregulator. As used herein, the term "toehold switch" generally refers to a regulator of gene expression, configured to repress or activate translation of an open reading frame and thus production of a protein. In some cases, toehold switches (also known as riboregulators) activate or repress gene expression in response to the presence or absence of cognate RNAs. Gene regulation is achieved through the presence of a regulatory nucleic acid element (the cis-repressive RNA or crRNA) within the 5' untranslated region (5' UTR) of an mRNA molecule. The nucleic acid element forms a hairpin structure comprising a stem domain and a loop domain through complementary base pairing.

Figure 1B:
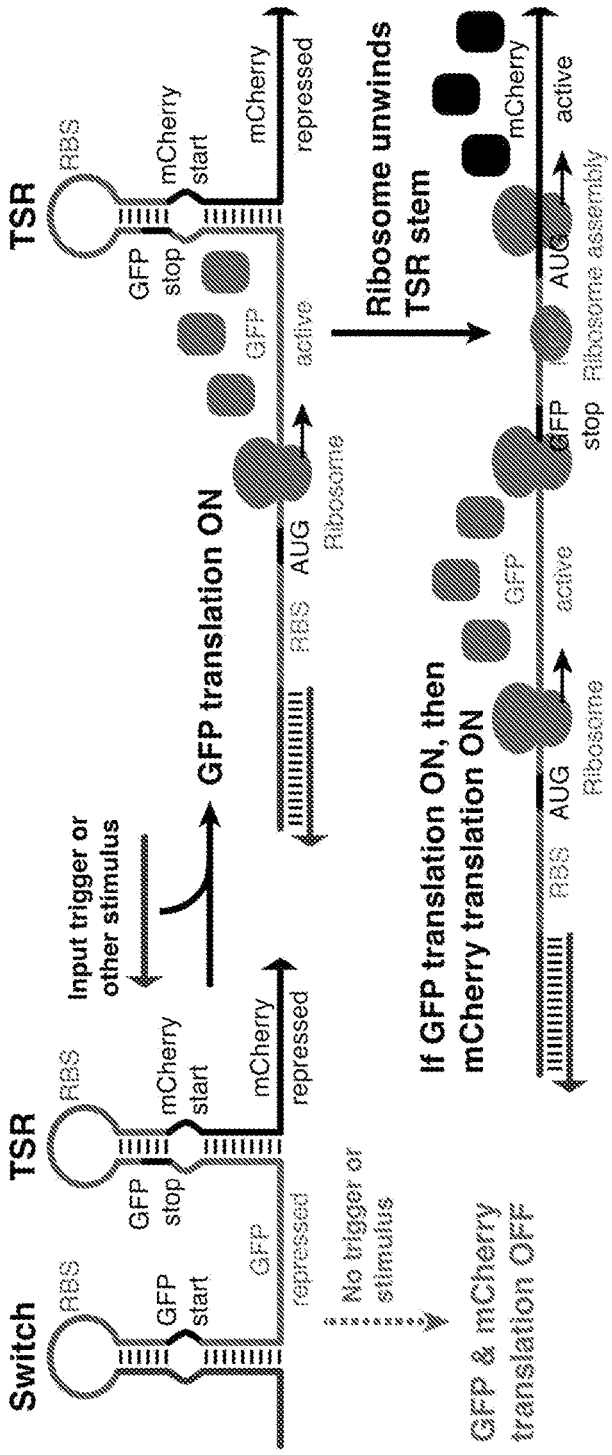

Referring to FIGS. 1A-1B, a 5' single-stranded region called a toehold is used to initiate a hybridization reaction with a trigger RNA with the complementary sequence A* to the A sequence in the switch RNA. The RNA sensing element of the toehold switch is an RNA hairpin located just upstream of a desired output gene. The RNA stem-loop structure of the hairpin, formed through complementary base pairing, is responsible for sensing of the target RNA. This hairpin sequesters within its loop a ribosomal binding site (RBS) and, within a bulge, a start codon for the output gene. The RBS and start codon for the output gene are positioned within the loop and within a bulge on the stem, respectively. Binding of a cognate trigger RNA to a toehold switch disrupts the switch RNA stem and exposes the RBS and start codon. The newly freed RBS and start codon can then enable translation of the downstream gene. When the trigger RNA binds to the single-stranded region at the 5' end (toehold), the stem will gradually unwind, and the RBS and the start codon will be exposed. As result, the translation of the output gene is activated.

As used herein, the term "hairpin" or "hairpin structure" refers to an intramolecular structure of a nucleic acid sequence at the chosen assay temperature mediated by hybridization of complementary sequences at the 5'- and the 3'-end of the nucleic acid sequence. As used herein, the terms "trigger" or "trigger sequence" refer to a RNA molecule capable of binding to the single-stranded regions immediately upstream and downstream of the switch RNA hairpin in order to form a structure that represses translational output.

Referring to FIG. 1B, a synthetic translation-sensing riboswitch (TSR) RNA device of the present disclosure comprises the same basic hairpin structure of the toehold switch. In one embodiment, the hairpin comprises an 18-nucleotide (nt) stem-forming domain and a 12-nt loop with a 3-nt bulge inside the stem domain for the output gene start codon (FIG. 1B). In other cases, the stem-forming domain will be shorter or longer than 18 nucleotides, where the length of a stem-forming domain may be measured from the first pair of complementary nucleotides to the last pair of complementary bases and includes mismatched nucleotides (e.g., pairs other than AT, AU, GC), nucleotides that form a bulge, or nucleotides that form a loop. The 3-nt bulge and the in-loop RBS advantageously provide more sequence design space such that either the input or output protein may retain its complete sequence while still providing low off-state expression. Outside of the RBS, the start codon, and the stop codon, the sequences of the TSR hairpins are constrained only by the designed secondary structure of the hairpin. This feature means that the native or original sequence for the 3' end of the input protein or the 5' end of the output protein can be incorporated directly into the TSR. Complementary sequences (or unpaired sequences in the bulge site) can then be used to ensure the TSR still has the desired secondary structure. Also within the hairpin domain of the TSR is a stop codon of the upstream ("input") gene, placed in a different reading frame than that of the downstream ("output") gene. Advantageously, this configuration ensures that the ribosome is very unlikely to produce a fusion protein of input and output genes even if it continues to translate the mRNA after encountering the stop codon.

When the input gene upstream of the TSR is not being translated, the RBS and start codon of the hairpin structure of the TSR remain sequestered and thus the output gene is not translated. However, when expression of the upstream gene occurs, the ribosome will translate through to the stop codon of the upstream gene and in turn cause the hairpin structure of the TSR to unwind. Once the hairpin structure of the TSR is disrupted, the RBS and start codon of the output gene are exposed, facilitating production of the output protein.

In one embodiment, provided herein is a synthetic nucleic acid molecule configured as a translation-sensing riboregulator, where the synthetic nucleic acid molecule comprises a first nucleotide sequence encoding a polypeptide, a translation-sensing riboswitch (TSR), and a second nucleotide sequence encoding a polypeptide, wherein the translation-sensing riboswitch comprises a stop codon of the first nucleotide sequence, a fully or partially double-stranded stem-forming domain, and translation initiation elements of the second nucleotide sequence.

In some cases, the nucleic acid encoding the first polypeptide is derived (e.g., obtained) from the genome of an organism of interest. In such cases, the TSR can be adjusted to accommodate the native sequence (including the stop codon) by changing sequences of the RBS, start codon, and second polypeptide to form the required secondary structure.

It will be understood that various structures of the TSR can be shortened or lengthened to modulate protein output and, in turn, dynamic range of synthetic nucleic acid device provided herein. For example, in some cases the length of loop domain is increased or decreased to alter reaction thermodynamics. In some embodiments, the stem domain of the TSR hairpin structure can be as small as 7 bps, but in some cases will be longer than 30 bps, including 31, 32, 33, or more base pairs in length. In some embodiments, the loop domain of the TSR hairpin structure can be as small as 6 nts, but in some cases will be longer than 30 nts, including 31, 32, 33, or more nucleotides in length. In some embodiments, the bulge region of the TSR hairpin structure can be eliminated, but in some cases will be longer than 4 nts on either side of the stem, including 5, 6, or 7 nucleotides in length. In some embodiments, the loop domain may include the start codon and the RBS. In other cases, the loop domain may include the start codon and either none or a portion of the RBS. In these cases, the RBS or a portion of it would be included in the stem of hairpin. The stop codon can be positioned at many different potential locations in the TSR hairpin structure. The position of first nucleotide in the stop codon can range from the $4^{th}$ base pair from the bottom of the stem on the 5' side through to the $4^{th}$ nucleotide after the bottom of the stem on the 3' side. The stop codon must be positioned in the same reading frame of the input protein, but it can either be in frame or out of frame of the output protein without affecting the function of the TSR. In some cases, one or more domains of the TSR are complementary to a naturally occurring RNA. In other cases, one or more domains of the TSR are complementary to a non-naturally occurring RNA. As used herein, the term "bulge" refers to a region of non-complementarity. It will be understood that the term "bubble" implies no specific shape of said region, although in some embodiments it is shaped as a bubble. In some cases, TSRs comprise synthetic (engineered) molecules. In other cases, TSRs are designed to contain endogenous, naturally occurring RNAs or regions thereof. See, for example, U.S. 2015/0275203. Complementarity of two sequences is generally determined by dividing the total number of nucleotides that participate in complementary base pairs (GC, AU, AT) when the sequences are aligned to produce the maximum number of complementary base pairs, counting all nucleotides in the two sequences (including those in bulges, mismatches, or inner loops) by the total number of nucleotides contained in both sequences. For example, consider two sequences of 19 and 20 nucleotides in length in which alignment to produce the maximum number of complementary base pairs results in 16 base pairs, 1 inner loop of 2 nucleotides, 1 mismatch, and 1 bulge (in the sequence with 20 nucleotides). The percent complementarity of the two sequences is $[(16+17)/39] \times 100$. It will be appreciated that complementarity may be determined with respect to the entire length of the two sequences or with respect to portions of the sequences. As used herein, two sequences are considered "substantially complementary" herein if their complementarity is at least 50%.

As shown in FIG. 1B, the TSR can be operably linked to a nucleotide sequence of interest that is 3' to the toehold switch. In some cases, the nucleotide sequence encodes a polypeptide of interest such as, for example, a metabolic enzyme. In other cases, the nucleotide sequence encodes a reporter polypeptide such as a detectable reporter polypeptide (e.g., an *E. coli* lacZ reporter element encoding β-galactosidase) that is 3' to the toehold switch. As used herein, the term "operably linked" refers to a relationship between two nucleic acid sequences wherein the production or expression of one of the nucleic acid sequences is controlled by, regulated by, modulated by, etc., the other nucleic acid sequence. Genetic elements appropriate for the methods provided herein include, without limitation, nucleotide sequences encoding enzymatic reporters (e.g., β-galactosidase, alkaline phosphatase, DHFR, CAT), fluorescent or chemiluminescent reporters (e.g., GFP variants, mCherry, luciferase, e.g., luciferase derived from the firefly (*Photinus pyralis*) or the sea pansy (*Renilla reniformis*) and mutants thereof), etc.

Figure 3:
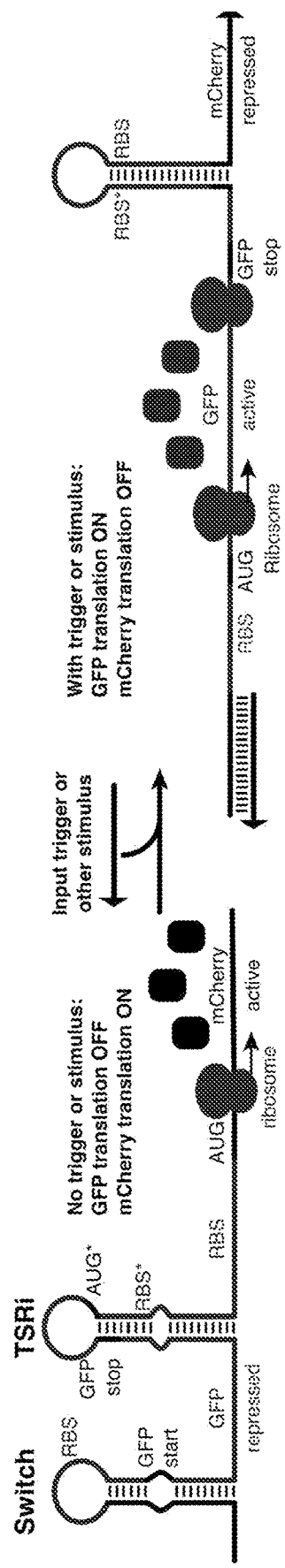
FIG. 3 presents a design schematic of synthetic translation-sensing riboswitch inverter ("TSRi"). A toehold switch is located upstream of the input GFP gene, followed by a translation-sensing riboswitch inverter, consisting of a hairpin containing the stop codon of the first gene (GFP), and reverse compliment sequences of the RBS and start codon, RBS* and AUG* respectively. When the system is supplied with cognate input trigger of the toehold switch, the first RBS is exposed and translation of the first gene begins as the ribosome travels down the transcript. Finally, the progress of the ribosome unwinds the TSRi hairpin and exposes the reverse compliment sequences of the RBS and start codon. This event enables the formation of a hairpin downstream of the inverter hairpin, and represses the expression of mCherry.

In another aspect, provided herein is an "inverted" TSR system in which translation of an active output gene is repressed when the input gene is translated. As depicted in FIG. 3, an inverted TSR system can comprise a ribosome-sensing hairpin element, however, this element is now upstream of an exposed RBS and a start codon that enables translation of an output gene in the absence of upstream translation. Referring to FIG. 3, an exemplary inverted TSR system comprises toehold switch located upstream of an input gene (GFP in this example), followed by a translation-sensing riboswitch inverter ("TSRi") hairpin-containing element containing the stop codon of the input gene, and reverse compliment sequences of the RBS and start codon (RBS* and AUG* respectively). In the absence of a trigger RNA (i.e., no trigger RNA bound to a toehold switch), translation of the input gene is suppressed, while translation of an output gene (mCherry in this example) located downstream of the TSRi is active ("ON"). When the system is supplied with cognate trigger of the toehold switch, the first RBS is exposed and translation of the input gene begins as the ribosome travels down the transcript. Progress of the ribosome unwinds the TSRi hairpin and exposes the reverse compliment sequences of the RBS and start codon. This event enables the formation of a hairpin downstream of the inverter hairpin, and represses the expression of the output gene.

In some cases, a synthetic nucleic acid molecule provided herein comprises a first nucleotide sequence encoding a first polypeptide, a translation-sensing riboswitch inverter (TSRi), and a second nucleotide sequence encoding a second polypeptide, where the TSRi comprises a stop codon of the first nucleotide sequence, a fully or partially double-stranded stem-forming domain, and translation initiation elements of the second nucleotide sequence, and where the TSRi is configured to adopt a translationally inactive OFF state when the first polypeptide is being translated.

Figures 4A, 4B, 4C:
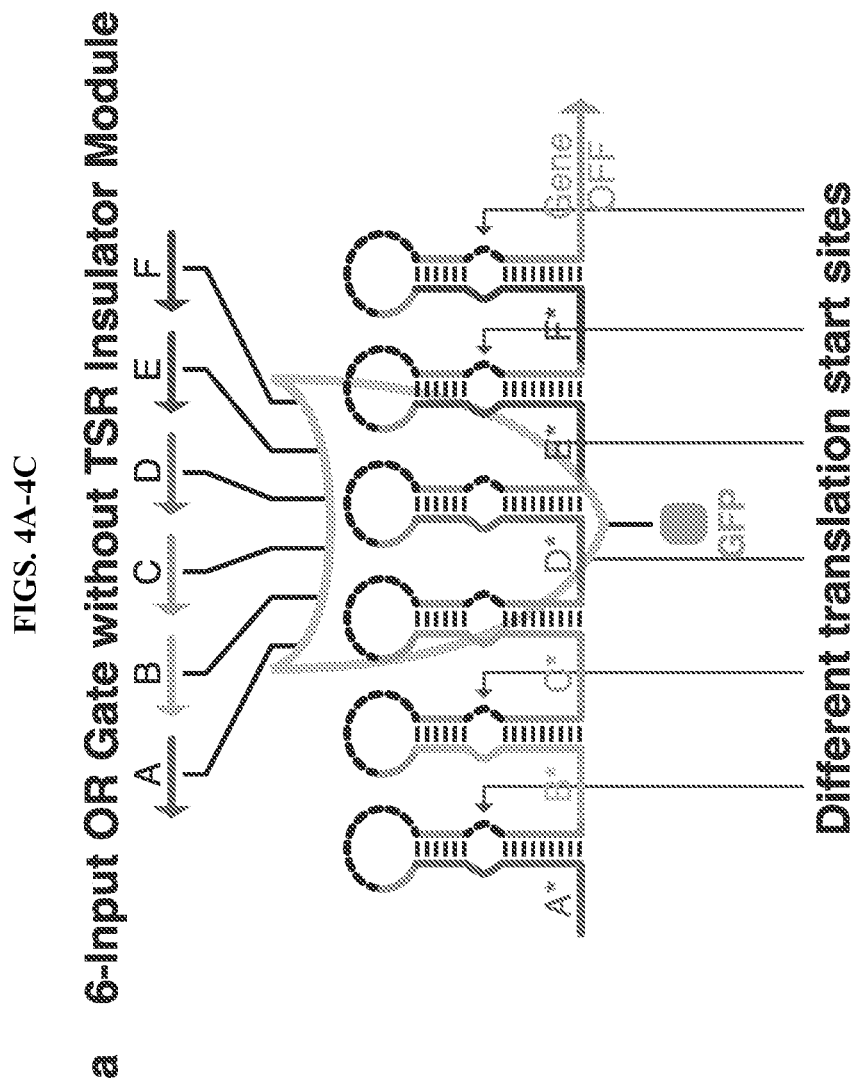
FIGS. 4A-4C illustrate an exemplary use of TSRs to insulate RNA circuit elements. (A) Schematic of a standard OR gate RNA containing six toehold switch sensor modules upstream of an output gene being regulated. Each of the toehold switches is in the same reading frame and contains RBS and start codon domains (represented as dashed black lines) for translation initiation. Cognate input RNAs (A through F) can bind to their complementary toehold switch sensors (A* through F*) to activate translation of the output gene. Since translation begins at different sites depending on the input RNA used, the output protein can have many additional residues encoded by the sequences of the downstream sensor modules. (B) Schematic of a 6-input OR gate insulated by a TSR module. The 6-input OR gate can be identical to that used in panel a, except that a TSR is added immediately before the output gene. Insulation by the TSR allows the output protein to be translated from a single start site to improve system performance and reliability. (C) ON/OFF GFP levels obtained from a TSR-insulated 6-input OR gate. The OR gate operates successfully for all six cognate RNAs A through F and provides low leakage levels for non-cognate RNAs G and H.

While the following examples of the application of the synthetic translation-sensing riboswitches provided herein are given, they are for illustration only and not intended to limit the claims. Uses of synthetic translation-sensing riboswitches include, without limitation, detecting translation of a target polypeptide for bioimaging and/or diagnostic applications and for modulating biochemical pathways for metabolic engineering applications. A TSR can be employed for detecting translation of a target polypeptide by inserting the TSR and a desired reporter gene (e.g., GFP, mCherry, β-galactosidase) downstream of the sequence of the target polypeptide. This insertion can occur into the chromosome of the organism of interest or the target polypeptide-TSR-reporter cassette can be expressed exogenously from a plasmid. When the resulting bicistronic mRNA is expressed, translation of the target polypeptide will cause the TSR to activate translation of the reporter protein. This reporter protein can then be detected via microscopy or using optical methods, such as in a microplate reader. Thus, TSRs can be used to measure in real-time the translation of polypeptides. This capability is of particular interest for proteins that undergo post-transcriptional regulation. A TSR can be employed for diagnostic applications in the contexts shown in FIGS. 4 and 5. For instance, a diagnostic device may be designed to detect a set of 6 different nucleic acid sequences from a pathogen using the toehold-switch-based gate RNA system shown in FIG. 4A. However, output from the system in FIG. 4A is variable because of the use of multiple translation start sites. To eliminate the variable translation start site problem, a TSR can be inserted downstream of the sensor region and upstream of the reporter so that activation of the gate RNA produces a reporter protein that has only a single possible translation start site. Thus, use of the TSR can lead to more reliable sensing of different nucleic acids in a diagnostic. For the diagnostic application of the TSR in FIG. 5, multiple TSRs are chained together downstream of a reporter gene that is activated by a toehold switch. After each TSR is another reporter protein that can be detected directly (e.g., through fluorescence) or via its action on a substrate (e.g., colorimetric substrate cleavage reaction). When the reporter gene regulated by the toehold switch is activated via binding of a target nucleic acid, a set of additional reporters regulated by the chain of TSRs is produced. If these TSR reporters are the same protein, this phenomenon will lead to increased production of the reporter protein and increase the speed and/or the sensitivity of the diagnostic test. If these TSR reporters are different, they can be used to produce different combinations and amounts of reporters depending on the target nucleic acid detected. By monitoring the combinations of reporters produced, test multiplexing can be improved so that multiple unique nucleic acids, potentially from different pathogens (e.g., Zika virus, dengue virus, chikungunya virus, West Nile virus, etc.) can be detected in a single diagnostic reaction. This type of multiplexing would expand diagnostic functionality and reduce its cost.

In another embodiment, TSRs are used to detect the response of an RNA to a stimulus and act as a sensor system. For example, a TSR can be designed to bind a small molecule such as ATP. In the presence of ATP, the first polypeptide is translated. For instance, you could have a riboswitch that binds to a small molecule (e.g., ATP) to translate the first polypeptide. Since riboswitch behavior can be very sensitive to RNA sequence, it is advantageous in some cases to couple the riboswitch to a distant TSR-second polypeptide cassette for improved sensor reliability and performance.

In some cases, TSRs are used for methods of regulating expression of one or more enzymes, including entire metabolic pathways. In such cases, the method includes inserting one or more TSRs into a nucleic acid comprising nucleotide sequences encoding one or more enzymes (e.g., each enzyme in a metabolic pathway). The inventors have demonstrated that the TSRs provided herein yield an average 15-fold change of expression. As used herein, the terms "expressing," "expression," or "express" refer to the production of a gene product (e.g., an mRNA transcript from a nucleic acid sequence encoding thereof). As used herein, the terms "gene product" and "expression product" generally refer to an RNA transcribed from the gene or a polypeptide encoded by an RNA transcribed from the gene. Thus a regulatory element, environmental condition, stimulus, etc., that alters the level of transcription or the stability of an RNA transcribed from a gene or alters its ability to serve as a template for translation will be said to alter expression of the gene. Similarly, a regulatory element, environmental condition, stimulus, etc., that alters the level of translation or stability of a polypeptide translated from an RNA transcribed from the gene will be said to alter expression of the gene.

Figure 5:
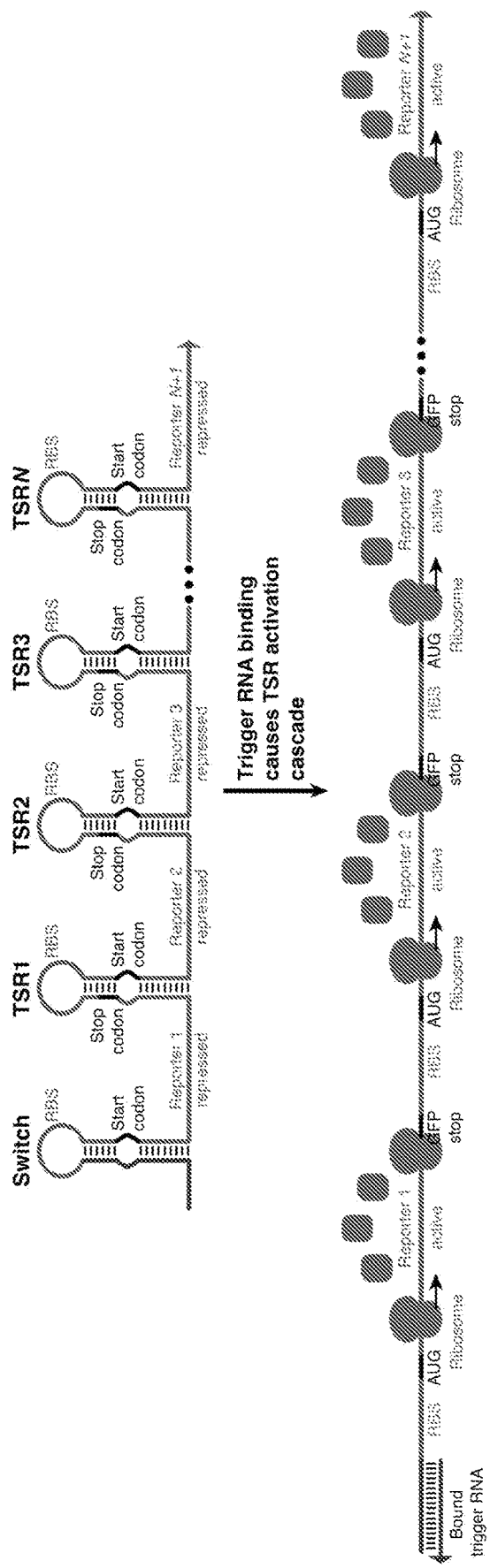
FIG. 5 illustrates an implementation of a TSR cascade reaction. An array of TSR modules can be constructed within the same RNA transcript to establish a TSR cascade reaction. In the system depicted, a toehold switch is used to regulate the first reporter protein and a downstream chain of TSRs detects activation of the toehold switch. When a trigger RNA binds to the polycistronic mRNA, reporter 1 translation activates TSR1. In turn, reporter 2 translation activates TSR2, and so on. The net result is that multiple reporter mRNA regions are activated in response to a single RNA binding event. The functionality can be used to activate metabolic pathways and to amplify signals from RNA binding.

In some embodiments, multiple TSRs are used in conjunction to regulate expression of a target gene. For example, an array of TSR modules can be constructed within the same construct to establish a TSR cascade reaction. As depicted in FIG. 5, a TSR cascade construct can comprise a plurality of TSRs located downstream of a toehold switch. In such a configuration, upon binding of a trigger RNA to the toehold switch, reporter 1 translation activates TSR1. In turn, reporter 2 translation activates TSR2, and so on. The net result is that multiple reporter mRNA regions are activated in response to a single RNA binding event. In this manner, the plurality of translation-sensing riboswitches enable expression of multiple genes to be coupled. This functionality can be used to activate metabolic pathways and to amplify signals from RNA binding.

In another embodiment, provided herein is a plurality of TSRs that form an innovative diagnostic platform. For example, TSR cascades comprising TSRs and/or TSRi can be used to amplify detection signals in a diagnostic device.

In another aspect, provided herein are translation-sensing riboregulators comprising translation-sensing riboswitches as well as inverted TSRs (TSRi). It will be advantageous in some cases to couple one or more translational inverters to one or more TSRs. For example, coupled TSRs and TSRi could be used to investigate post-transcriptional regulation and/or to modulate (activate or deactivate) metabolic pathways in living cells. Biochemical production of compounds in metabolic engineering often requires endogenous genes and pathways to be knocked out so that metabolite flux is only directed towards production of the desired compound. However, knocking out these genes often reduces strain growth rate and results in sub-optimal production. Alternatively, using systems of TSRs and TSRi it will be possible to dynamically turn on or off different metabolic pathways in response to a stimulus, such as the expression of an endogenous RNA or the addition of an inducer (e.g., IPTG). An endogenous RNA, for instance, can be upregulated when the cells reach stationary phase and can devote their full activity to production of the target chemical. An example of this approach is in the production of glucaric acid, which co-opts glucose from the glycolysis pathway (see for review, for example, T. K. Moon et al., *Appl. Env. Microbiol* 75, 589-595 (2009)). In this example, critical glycolysis pathway enzymes and glucaric acid pathway enzymes can both be regulated using their own sets of TSRs such that translation of one of the first gene in the pathway triggers translation of the remaining pathway components. TSR-linked cassettes for both pathways can be expressed in the same mRNA and a TSRi used to interface the input glucaric acid pathway with the output glycolysis pathway. A toehold switch can be inserted upstream of the first gene of the glucaric acid pathway so that the pathway is activated by an endogenous or exogenous trigger RNA. In the absence of the trigger RNA, the TSRi in the polycistronic mRNA will be active and thus translation of the glycolysis pathway components will occur. When the trigger RNA is present, the glucaric acid pathway components will be translated. Translation of the final gene of the glucaric acid pathway will in turn cause the TSRi to halt translation of the first gene in the glycolysis pathway, thereby shutting off expression of the remaining genes in the pathway. Using this approach, production of multiple pathway enzymes can be turned on or off dynamically in response to intracellular cues.

In some cases, TSRs are incorporated into complex, multi-input logic circuits. For diagnostics purposes, multi-input logic circuits can be used to increase assay specificity or sensitivity. For instance, a NOT-AND ("NAND") expression can reduce false positives by detecting the translation of more than one gene in a given sample. A NOT-OR ("NOR") expression can reduce false negatives by sensing translation of more than one gene in the same sample. In vivo, a multi-input logic circuit can be used to sense the translation of one or more polypeptides produced by a prokaryote in response to environment stresses. Such a protein expression signature can be used to modulate production of enzymes or identify cells that are susceptible to antibiotics or screen for new antibiotic compounds. In addition, the circuits that sense a set of polypeptides expressed by the host could be used to generate whole-cell biosensors that detect toxic chemicals in the environment.

For example, TSRs can be inserted into gate RNAs used for molecular logic computation to insulate information processing elements from the sequence of the output protein. TSRs are very useful tools for accomplishing this insulation function as they can detect activation of a gate RNA and use this stimulus to initiate translation of an unrelated output protein. As depicted in FIG. 4B, a TSR module can be deployed as an insulator within a 6-input OR gate. The TSR is added to the gate RNA downstream of the final sensor module in the transcript. Thus, activation of any of the upstream sensors can cause the ribosome to unwind the TSR and trigger translation of an output gene that lacks any additional N-terminal residues and has the same sequence, no matter which sensor is used to turn ON the system. As described in the Examples that follow, input OR gates insulated by a TSR module operates successfully for all cognate RNAs and provides low leakage levels for non-cognate RNAs.

By way of example, a multi-input logic circuit can be used in vivo to detect a set of proteins produced by a prokaryote in response to a stimulus such as an environment stress (e.g., physical stress (e.g., heat, anoxia), chemical stress (e.g., chemical compound, toxin, candidate therapeutic agent)). The resulting protein expression signature detected by the logic circuit can be used to, for example, identify cells that are susceptible to antibiotics or screen for new antibiotic compounds. In addition, the circuits that sense a set of proteins expressed by a host cell could be used to generate whole-cell biosensors that detect toxic chemicals in the environment.

In some cases, a method for detecting response of a cell to a stimulus comprises (i) introducing into a cell a synthetic nucleic acid molecule comprising a first nucleotide sequence encoding a first polypeptide, a translation-sensing riboswitch (TSR), and a second nucleotide sequence encoding a second polypeptide, wherein the translation-sensing riboswitch comprises a stop codon of the first nucleotide sequence, a fully or partially double-stranded stem-forming domain, and translation initiation elements of the second nucleotide sequence; (ii) detecting an expression level of each of the first and second polypeptides in the cell; (iii) exposing the cell comprising the introduced molecule to a stimulus; and (iv) detecting an expression level of each of the first and second polypeptides in the exposed cell, where an increase in expression of the second polypeptide following exposure relative to its expression prior to exposure indicates that translation of the first polypeptide was upregulated in the presence of the stimulus, and where a decrease in expression of the second polypeptide following exposure relative to its expression prior to exposure indicates that translation of the first polypeptide was downregulated in the presence of the stimulus.

In some cases, a TSRi system provided herein can also be used to insulate sensor modules from the output protein. When TSRi systems are used in this context, they can also invert the function of the gate RNA transforming an OR gate RNA into a NAND circuit, or transforming a NAND gate RNA into an OR circuit.

As used herein, the terms "synthetic" and "engineered" are used interchangeably and refer to a non-naturally occurring nucleic acid molecule that has been created or modified by the hand of man (e.g., using recombinant DNA technology) or is derived from such a molecule (e.g., by transcription, translation, etc.). A nucleic acid molecule may be similar in sequence to a naturally occurring nucleic acid but typically contains at least one artificially created insertion, deletion, inversion, or substitution relative to the sequence found in its naturally occurring counterpart. Likewise, a cell that contains a synthetic or engineered nucleic acid is considered to be an engineered cell.

Nucleic acids generally refer to polymers comprising nucleotides or nucleotide analogs joined together through backbone linkages such as but not limited to phosphodiester bonds. Nucleic acids include deoxyribonucleic acids (DNA) and ribonucleic acids (RNA) such as messenger RNA (mRNA), transfer RNA (tRNA), etc. Nucleic acids may be single-stranded, double-stranded, and also tripled-stranded. The nucleic acids of the invention, including the translation-sensing riboswitch (TSR), may be provided or present in a larger nucleic acid. The larger nucleic acid may be responsible for the transcription and thus production of the TSR, as described in Example 1, for example. The larger nucleic acid may comprise a nucleotide sequence that is transcribed to produce the TSR. For convenience, the invention may refer to the larger nucleic acid as comprising the TSR although it is to be understood that in practice this intends that the larger nucleic acid comprises a sequence that encodes the TSR. Such encoding sequences may be operably linked to other sequences in the larger nucleic acid such as but not limited to origins of replication. As used herein, "operably linked" refers to a relationship between two nucleic acid sequences wherein the production or expression of one of the nucleic acid sequences is controlled by, regulated by, modulated by, etc., the other nucleic acid sequence. For example, the transcription of a nucleic acid sequence is directed by an operably linked promoter sequence; post-transcriptional processing of a nucleic acid is directed by an operably linked processing sequence; the translation of a nucleic acid sequence is directed by an operably linked translational regulatory sequence; the transport or localization of a nucleic acid or polypeptide is directed by an operably linked transport or localization sequence; and the post-translational processing of a polypeptide is directed by an operably linked processing sequence. Preferably a nucleic acid sequence that is operably linked to a second nucleic acid sequence is covalently linked, either directly or indirectly, to such a sequence, although any effective association is acceptable.

The term "detect" or "detection" as used herein indicates the determination of the existence, presence or fact of a target or signal in a limited portion of space, including but not limited to a sample, a reaction mixture, a molecular complex and a substrate including a platform and an array. Detection is "quantitative" when it refers, relates to, or involves the measurement of quantity or amount of the target or signal (also referred as quantitation), which includes but is not limited to any analysis designed to determine the amounts or proportions of the target or signal. Detection is "qualitative" when it refers, relates to, or involves identification of a quality or kind of the target or signal in terms of relative abundance to another target or signal, which is not quantified. An "optical detection" indicates detection performed through visually detectable signals: fluorescence, spectra, or images from a target of interest or a probe attached to the target.

The term "express" and "expression" means allowing or causing the information in a gene or DNA sequence to become manifest, for example producing RNA (such as rRNA or mRNA) or a protein by activating the cellular functions involved in transcription and translation of a corresponding gene or DNA sequence. A DNA sequence is expressed by a cell to form an "expression product" such as an RNA (a mRNA or a rRNA) or a protein. The expression product itself, such as the resulting RNA or protein, may also be said to be "expressed" by the cell.

A "polypeptide" is a chain of chemical building blocks called amino acids that are linked together by chemical bonds called "peptide bonds". The term "protein" refers to polypeptides that contain the amino acid residues encoded by a gene or by a nucleic acid molecule such as an mRNA or a cDNA, transcribed from that gene either directly or indirectly. Optionally, a protein may lack certain amino acid residues that are encoded by a gene or by an mRNA. For example, a gene or mRNA molecule may encode a sequence of amino acid residues on the N-terminus of a protein, such as a signal sequence, that is cleaved from, and therefore may not be part of, the final protein. A protein or polypeptide, including an enzyme, maybe a "native" or "wild-type", meaning that it occurs in nature; or it may be a "mutant", "variant" or "modified", meaning that it has been made, altered, derived, or is in some way different or changed from a native protein or from another mutant.

A "gene" is a sequence of nucleotides which code for a functional "gene product". Generally, a gene product is a functional protein. However, a gene product can also be another type of molecule in a cell, such as an RNA and more specifically either a tRNA or a rRNA. For the purposes of the present invention, a gene product also refers to an mRNA sequence which may be found in a cell. For example, measuring gene expression levels according to the invention may correspond to measuring mRNA levels. A gene may also comprise regulatory, non-coding, sequences as well as coding sequences.

A variety of different gene expression protocols, including arrays based protocols, are known to those of skill in the art, including those described in: EP 0 328 829 B1 and U.S. Pat. Nos. 5,468,613; 5,580,726; 5,599,672; 5,512,462; 5,162,209 and 5,162,209, the disclosures of which are herein incorporated by reference. Methods of analyzing differential gene expression are also described in Maniatis, et al., Molecular Cloning, A Laboratory Manual, (Cold Spring Harbor Press, Cold Spring Harbor, N.Y.)(1989); Nucleic Acid Hybridization, A Practical Approach (Hames, B. D., and Higgins, S. J. eds, IRL Press, Oxford)(1985); WO 95/21944; Chalifour, et al., Anal. Biochem. (1994) 216: 299-304; Nguyen et al., Genomics (1995) 29: 207-216; Pietu et al., Genome Res. (1996) 6: 492-503; and Zhao et al., Gene (1995) 166: 207-213.

Nucleic acids and/or other moieties of the invention may be isolated. As used herein, "isolated" means separate from at least some of the components with which it is usually associated whether it is derived from a naturally occurring source or made synthetically, in whole or in part.

Nucleic acids and/or other moieties of the invention may be purified. As used herein, purified means separate from the majority of other compounds or entities. A compound or moiety may be partially purified or substantially purified. Purity may be denoted by a weight by weight measure and may be determined using a variety of analytical techniques such as but not limited to mass spectrometry, HPLC, etc.

It is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

As used herein, the singular forms "a", "an" and "the" include plural referents unless the context clearly dictates otherwise. "And" as used herein is interchangeably used with "or" unless expressly stated otherwise. It is also to be noted that the terms "comprising", "including", and "having" can be used interchangeably.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

In preferred embodiments, the terms "about" and "approximately" shall generally mean an acceptable degree of error for the quantity measured given the nature or precision of the measurements. Typical, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. Numerical quantities given herein are approximate unless stated otherwise, meaning that the term "about" or "approximately" can be inferred when not expressly stated.

All embodiments within and between different aspects of the invention can be combined unless the context clearly dictates otherwise. It should also be understood that, unless clearly indicated to the contrary, in any methods claimed herein that include more than one step or act, the order of the steps or acts of the method is not necessarily limited to the order in which the steps or acts of the method are recited.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. The present invention has been described in terms of one or more preferred embodiments, and it should be appreciated that many equivalents, alternatives, variations, and modifications, aside from those expressly stated, are possible and within the scope of the invention. The invention will be more fully understood upon consideration of the following non-limiting Example.

EXAMPLE

The invention will be more fully understood upon consideration of the following non-limiting Example. This example describes translation-sensing riboswitches and uses thereof.

Bacteria commonly express enzymes in metabolic pathways using polycistronic mRNAs that encode the sequences of multiple genes. Translation of these genes is governed by a phenomenon known as translational coupling, which ties the expression levels of downstream genes within the mRNA to those located upstream. The atp operon in *E. coli*, for instance, provides a well-known example of translational coupling. In this operon, translation of the downstream gene (atpA) is normally blocked by a hairpin secondary structure at the end of the upstream gene (atpH). The inhibitory mRNA hairpin only opens to allow translation of atpA when the upstream atpH is being translated[1].

Despite their widespread use in nature, it has been difficult to rationally engineer the translational coupling between genes on the same polycistronic transcript and efforts to engineer synthetic translational couplers remain in their infancy. The translational efficiency of the downstream gene is strongly dependent on the secondary structure of the ribosomal binding site (RBS) and start codon, yet these features change with each modification to nearby sequences at the end of the upstream gene. Moreover, translational coupling is tied to the procession of the ribosome along the mRNA, a dynamic ribonucleoprotein interaction that is far harder to model than RNA secondary structures along. Recently, Salis and coworkers developed a biophysical model to predict the behavior of translational couplers in *E. coli*.[4] Although their coupling systems offered predictable performance, multiple designs displayed leakage in downstream gene expression, potentially limiting their use in applications such as metabolic engineering and in vivo logic systems. Furthermore, they required modifications to the sequences of both the upstream and downstream genes, which could affect their folding and function when expressed.

In this Example, we describe a new class of translational couplers called translation-sensing riboswitches (TSRs). TSRs monitor the movement of the ribosome along an mRNA to activate gene expression only in response to translation of the upstream gene. Importantly, they employ the same RNA secondary structure, simplifying the design process and improving device modularity, and only require modifications to the sequence of either the upstream or downstream gene. Using the same base TSR design, we have validated 24 functional riboswitches (see Table 1) that display low leakage and increase expression of a downstream mCherry reporter by 15-fold on average in response to upstream translation. We found that expression levels between the upstream and downstream genes were strongly correlated when coupled via TSRs. Insertion of TSRs into gate RNAs used for molecular logic computation is further used to insulate information processing elements from the sequence of the output protein. In addition, we designed TSR inverters that respond to translation by turning off translation of a downstream gene and conceived of TSR cascades that can be used to amplify detection signals in diagnostic devices. By inserting TSRs upstream of genes or integrating them into more complex genetic circuits, our systems not only allow the activation or deactivation of multiple genes in response to single post-transcriptional activation event, but also enable RNA-based regulation without requiring any changes to the output protein sequence.

RESULTS

Translation-Sensing Riboswitch Design

The base design of the TSRs is inspired by the toehold switch, a recently developed riboregulator[3] (FIG. 1A). The toehold switch only activates translation upon binding a cognate trigger RNA. The RNA sensing element of the toehold switch is an RNA hairpin located just upstream of a desired output gene. This hairpin sequesters within its loop the ribosomal binding site (RBS) and, within a bulge, the start codon for the output gene. A single-stranded region at the 5' end of the hairpin referred to as a toehold is used to initiate the interaction with the trigger RNA. When the trigger RNA is expressed, it hybridizes with the toehold region of the switch, gradually unwinds the stem-loop (hairpin) structure of the switch, and eventually exposes the RBS and the start codon (AUG) of the downstream gene. The exposed RBS and start codon are now available for the ribosome assembly to the mRNA to initiate translation. The novel repression mechanism of the switch enables it to detect nearly arbitrary sequences and provides very low off-state expression in the absence of the trigger.

Building on these results, we hypothesized that the stem unwinding used to activate the toehold switch could be coupled to other molecular cues beyond RNA-RNA hybridization, namely the movement of a translating ribosome. Thus, TSRs adopt the same basic hairpin structure of the toehold switch. This hairpin consists of an 18-nt stem and a 12-nt loop with a 3-nt bulge inside the stem for the output gene start codon (FIG. 1B). The 3-nt bulge and the in-loop RBS gives us more design space (arbitrary sequences in gray in FIG. 1B) enabling either the input or output protein to retain its complete sequence while still providing low off-state expression. Within the hairpin is also the stop codon of the upstream or input gene in a different reading frame than that of the downstream output gene. This design feature ensures that the ribosome is very unlikely to produce a fusion protein of input and output genes even if it continues to translate the mRNA after encountering the stop codon. When the input gene upstream of the TSR is not being translated, the RBS and start codon of the TSR hairpin remain sequestered and thus the output gene is not translated. However, when expression of the upstream gene occurs, the ribosome will translate through to the stop codon of the upstream gene and in turn cause the TSR hairpin to unwind. Once the hairpin structure of the TSR is disrupted, the RBS and start codon of the output gene are exposed, facilitating production of the output protein.

To test the TSR mechanism, we constructed polycistronic plasmids expressing GFP as the input protein and mCherry, a red-fluorescent protein, as the output protein. The TSR was inserted in the region between the GFP input and mCherry output genes (FIG. 1B). Translation of the GFP input protein was regulated using a toehold switch. Inclusion of the toehold switch enabled us to regulate input GFP translation post-transcriptionally via a trigger RNA. This strategy ensured that translation of the output mCherry gene was due to post-transcriptional regulation by the TSR, rather than another effect such as aborted transcription. We then employed this system to test 24 TSRs with different sequences and systematically modified the intergenic distances between the input and output genes. TSR sequences are presented in Table 1. The intergenic distance was modulated by changing the position of the stop codon within the TSR hairpin. It is important to note that there are many other possible TSR designs that can be developed by changing the secondary structure of the TSR hairpin and changing the locations of the stop codon, RBS, and start codon. Alternative designs can be informed by existing riboregulators that activate translation in response to trigger RNA binding.

TABLE 1

| Name | TSR DNA Sequence Including Late Region of Input Gene and Early Region of Output Gene | TSR RNA hairpin |
|---|---|---|
| TSR_hpin01 | CATGGCATGGATGAACTATACAAAAGGCCTAACACTCCATCACTCCACCTCCACTCCCATCCCGCTCTGTTATCGGTTAAAGATAGAGGAGATTAACCATGAACAGAGCGAATTTAGCTGCCGCACAGAAAATGCGTAAA (SEQ ID NO: 1) | CGCUCUGUUAUCGGUUAAAGAUAGAGGAGAUUAACCAUGAACAGAGCG (SEQ ID NO: 2) |
| TSR_hpin02 | CATGGCATGGATGAACTATACAAAAGGCCTAACACTCCATCACTCCACCTCCACTCCCATCCGCACGTTCTATGTCTTAAGAACAGAGGAGATTAAGAATGAGAACGTGCAATTTAGCTGCCGCACAGAAAATGCGTAAA (SEQ ID NO: 3) | GCACGUUCUAUGUCUUAAGAACAGAGGAGAUUAAGAAUGAGAACGUGC (SEQ ID NO: 4) |
| TSR_hpin03 | CATGGCATGGATGAACTATACAAAAGGCCTACACTCCATCACTCCACCTCCACTCCCATCCCGTTCGCTTACCGTTATAGAACAGAGGAGATATAACATGAAGCGAACGAATTTAGCTGCCGCACAGAAAATGCGTAAA (SEQ ID NO: 5) | CGUUCGCUUACCGUUAUAGAACAGAGGAGAUAUAACAUGAAGCGAACG (SEQ ID NO: 6) |
| TSR_hpin04 | CATGGCATGGATGAACTATACAAAAGGCCTACACTCCATCACTCCACCTCCACTCCCATCCGCACTTGTCACCCTTATAGAACAGAGGAGATATAAGATGGACAAGTGCAATTTAGCTGCCGCACAGAAAATGCGTAAA (SEQ ID NO: 7) | GCACUUGUCACCCUUAUAGAACAGAGGAGAUAUAAGAUGGACAAGUGC (SEQ ID NO: 8) |
| TSR_hpin05 | CATGGCATGGATGAACTATACAAAAGGCCTAACACTCCATCACTCCACCTCCACTCCCATCCGCACTGTCTACCTAGTTATGATAGAGGAGATAACTAATGAGACAGTGCAATTTAGCTGCCGCACAGAAAATGCGTAAA (SEQ ID NO: 9) | GCACUGUCUACCUAGUUAUGAUAGAGGAGAUAACUAAUGAGACAGUGC (SEQ ID NO: 10) |
| TSR_hpin06 | CATGGCATGGATGAACTATACAAAAGGCCTAACACTCCATCACTCCACCTCCACTCCCATCCCGAATTTGCATGTAGTTACAATAGAGGAGATAACTAATGGCAAATTCGAATTTAGCTGCCGCACAGAAAATGCGTAAA (SEQ ID NO: 11) | CGAAUUUGCAUGUAGUUACAAUAGAGGAGAUAACUAAUGGCAAAUUCG (SEQ ID NO: 12) |
| TSR_hpin07 | CATGGCATGGATGAACTATACAAAAGGCCTAACACTCCATCACTCCACCTCCACTCCCATCCCGCTCTTGTACCTCGTTACAATAGAGGAGATAACGAATGACAAGAGCGAATTTAGCTGCCGCACAGAAAATGCGTAAA (SEQ ID NO: 13) | CGCUCUUGUACCUCGUUACAAUAGAGGAGAUAACGAAUGACAAGAGCG (SEQ ID NO: 14) |
| TSR_hpin08 | CATGGCATGGATGAACTATACAAAAGGCCTAACACTCCATCACTCCACCTCCACTCCCATCCGTTCCGTGTGTGCTGTTACAATAGAGGAGATAACAGATGACACGGAACAATTTAGCTGCCGCACAGAAAATGCGTAAA (SEQ ID NO: 15) | GUUCCGUGUGUGCUGUUACAAUAGAGGAGAUAACAGAUGACACGGAAC (SEQ ID NO: 16) |
| TSR_hpin09 | CATGGCATGGATGAACTATACAAAAGGCCTAACACTCCATCACTCCACCTCCACTCCCATCCGTCGGTTAGATGTCGTTACAATAGAGGAGATAACGAATGCTAACCGACAATTTAGCTGCCGCACAGAAAATGCGTAAA (SEQ ID NO: 17) | GUCGGUUAGAUGUCGUUACAAUAGAGGAGAUAACGAAUGCUAACCGAC (SEQ ID NO: 18) |
| TSR_hpin10 | CATGGCATGGATGAACTATACAAAAGGCCTAACACTCCATCACTCCACCTCCACTCCCATCCCAGTGTTAGATCATGTTACAATAGAGGAGATAACATATGCTAACACTGAATTTAGCTGCCGCACAGAAAATGCGTAAA (SEQ ID NO: 19) | CAGUGUUAGAUCAUGUUACAAUAGAGGAGAUAACAUAUGCUAACACUG (SEQ ID NO: 20) |
| TSR_hpin11 | CATGGCATGGATGAACTATACAAAAGGCCTACACTCCATCACTCCACCTCCACTCCCATCCGCACTTATTGCCTCGTTAGAATAGAGGAGATAACGAATGAATAAGTGCAATTTAGCTGCCGCACAGAAAATGCGTAAA (SEQ ID NO: 21) | GCACUUAUUGCCUCGUUAGAAUAGAGGAGAUAACGAAUGAAUAAGUGC (SEQ ID NO: 22) |

TABLE 1-continued

| Name | TSR DNA Sequence Including Late Region of Input Gene and Early Region of Output Gene | TSR RNA hairpin |
|---|---|---|
| TSR_hpin12 | CATGGCATGGATGAACTATACAAAAGGCCTAC ACTCCATCACTCCACCTCCACTCCCATCCCGCTT TATCATGGTCTTAGAACAGAGGAGATAAGACAT GGATAAAGCGAATTTAGCTGCCGCACAGAAAA TGCGTAAA (SEQ ID NO: 23) | CGCUUUAUCAUGGUCUU AGAACAGAGGAGAUAA GACAUGGAUAAAGCG (SEQ ID NO: 24) |
| TSR_hpin13 | CATGGCATGGATGAACTATACAAAAGGCCTAA CACTCCATCACTCCACCTCCACTCCCATCCGTA ATGTGTACCGCCTTAGAACAGAGGAGATAAGG CATGACACATTACAATTTAGCTGCCGCACAGAA AATGCGTAAA (SEQ ID NO: 25) | GUAAUGUGUACCGCCUU AGAACAGAGGAGAUAA GGCAUGACACAUUAC (SEQ ID NO: 26) |
| TSR_hpin14 | CATGGCATGGATGAACTATACAAAAGGCCTAC ACTCCATCACTCCACCTCCACTCCCATCCGCTA ATGTTACCTGTATAGAACAGAGGAGATATACAA TGAACATTAGCAATTTAGCTGCCGCACAGAAAA TGCGTAAA (SEQ ID NO: 27) | GCUAAUGUUACCUGUAU AGAACAGAGGAGAUAU ACAAUGAACAUUAGC (SEQ ID NO: 28) |
| TSR_hpin15 | CATGGCATGGATGAACTATACAAAAGGCCTAA CACTCCATCACTCCACCTCCACTCCCATCCGTCG TAAGCACCGTGTAAGAACAGAGGAGATTACAC ATGGCTTACGACAATTTAGCTGCCGCACAGAAA ATGCGTAAA (SEQ ID NO: 29) | GUCGUAAGCACCGUGUA AGAACAGAGGAGAUUA CACAUGGCUUACGAC (SEQ ID NO: 30) |
| TSR_hpin16 | CATGGCATGGATGAACTATACAAAAGGCCTAC ACTCCATCACTCCACCTCCACTCCCATCCGCAC GTAATACCCTGTTAGAACAGAGGAGATAACAG ATGATTACGTGCAATTTAGCTGCCGCACAGAAA ATGCGTAAA (SEQ ID NO: 31) | GCACGUAAUACCCUGUU AGAACAGAGGAGAUAA CAGAUGAUUACGUGC (SEQ ID NO: 32) |
| TSR_hpin17 | CATGGCATGGATGAACTATACAAAAGGCCTAA CACTCCATCACTCCACCTCCACTCCCATCCGCA CGTGTAATGCTGTTAGAATAGAGGAGATAACA GATGTACACGTGCAATTTAGCTGCCGCACAGAAA AATGCGTAAA (SEQ ID NO: 33) | GCACGUGUAAUGCUGUU AGAAUAGAGGAGAUAA CAGAUGUACACGUGC (SEQ ID NO: 34) |
| TSR_hpin18 | CATGGCATGGATGAACTATACAAAAGGCCTAC ACTCCATCACTCCACCTCCACTCCCATCCCGCTT GTATAGGCTGTTAAGACAGAGGAGATAACAGA TGATACAAGCGAATTTAGCTGCCGCACAGAAA ATGCGTAAA (SEQ ID NO: 35) | CGCUUGUAUAGGCUGUU AAGACAGAGGAGAUAA CAGAUGAUACAAGCG (SEQ ID NO: 36) |
| TSR_hpin19 | CATGGCATGGATGAACTATACAAAAGGCCTAA CACTCCATCACTCCACCTCCACTCCCATCCGCA CTTGTTCTAATCTTAGAACAGAGGAGATAAGAT ATGAACAAGTGCAATTTAGCTGCCGCACAGAA AATGCGTAAA (SEQ ID NO: 37) | GCACUUGUUCUAAUCUU AGAACAGAGGAGAUAA GAUAUGAACAAGUGC (SEQ ID NO: 38) |
| TSR_hpin20 | CATGGCATGGATGAACTATACAAAAGGCCTAC ACTCCATCACTCCACCTCCACTCCCATCCGCCTT GTATACTAACTTAAGACAGAGGAGATAAGTTAT GATACAAGGCAATTTAGCTGCCGCACAGAAAA TGCGTAAA (SEQ ID NO: 39) | GCCUUGUAUACUAACUU AAGACAGAGGAGAUAA GUUAUGAUACAAGGC (SEQ ID NO: 40) |
| TSR_hpin21 | CATGGCATGGATGAACTATACAAAAGGCCTAA CACTCCATCACTCCACCTCCACTCCCATCCCGCT CTGTTACCGTAATAGAACAGAGGAGATATTACA TGAACAGAGCGAATTTAGCTGCCGCACAGAAA ATGCGTAAA (SEQ ID NO: 41) | CGCUCUGUUACCGUAAU AGAACAGAGGAGAUAU UACAUGAACAGAGCG (SEQ ID NO: 42) |
| TSR_hpin22 | CATGGCATGGATGAACTATACAAAAGGCCTAC ACTCCATCACTCCACCTCCACTCCCATCCGCGT ATGGTATCGGTAAACGACAGAGGAGATTTACC ATGACCATACGCAATTTAGCTGCCGCACAGAAA ATGCGTAAA (SEQ DI NO: 43) | GCGUAUGGUAUCGGUA AACGACAGAGGAGAUU UACCAUGACCAUACGC (SEQ ID NO: 44) |
| TSR_hpin23 | CATGGCATGGATGAACTATACAAAAGGCCTAA CACTCCATCACTCCACCTCCACTCCCATCCGCA CTTGTTATGTCGTTAAGATAGAGGAGATAACGA ATGAACAAGTGCAATTTAGCTGCCGCACAGAA AATGCGTAAA (SEQ ID NO: 45) | GCACUUGUUAUGUCGUU AAGAUAGAGGAGAUAA CGAAUGAACAAGUGC (SEQ ID NO: 46) |

TABLE 1-continued

| Name | TSR DNA Sequence Including Late Region of Input Gene and Early Region of Output Gene | TSR RNA hairpin |
|---|---|---|
| TSR_hpin24 | CATGGCATGGATGAACTATACAAAAGGCCTAC ACTCCATCACTCCACCTCCACTCCCATCCGTTCC GCGTGTGCTCTATAAGTAGAGGAGAATAGAGA TGACGCGGAACAATTTAGCTGCCGCACAGAAA ATGCGTAAA (SEQ ID NO: 47) | GUUCCGCGUGUGCUCUA UAAGUAGAGGAGAAUA GAGAUGACGCGGAAC (SEQ IDNO: 48) |

In Vivo Testing of Translation-Sensing Riboswitches

To characterize in vivo performance of the TSRs, E. coli BL21 Star DE3 was used. Isopropyl β-D-1-thiogalactopyranoside (IPTG) was used to induce the expression of the switch RNA, containing the TSR and the toehold switch, and the trigger RNA. Switches and triggers were inserted into two different plasmids with kanamycin and ampicillin resistance, respectively. ON states were measured from the cells with switches and the cognate trigger RNA of the toehold switch, whereas the OFF states were measured from the cells with switches and their non-cognate trigger.

Figures 2A, 2B, 2C:
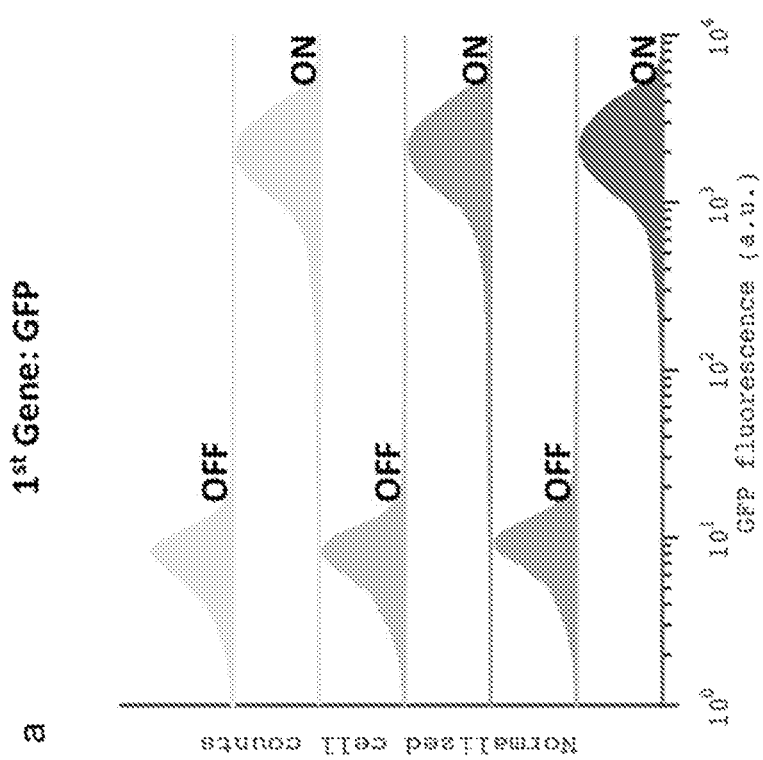
FIGS. 2A-2C present flow cytometry measurements of GFP and mCherry fluorescence. (A) Flow cytometry measurements were taken 5 hours after induction of protein expression in three biological replicates. OFF state (TSR with noncognate trigger) is displayed on top of the ON state (TSR+cognate trigger). Flow cytometry GFP fluorescence histograms for TSR hairpin 13 (TSR_hpin13) showed a dynamic range with ON/OFF ratio exceeding 200. (B) Flow cytometry mCherry fluorescence histograms for TSR hairpin 13 showed a clear difference between the ON and OFF with a ratio >30. (C) ON/OFF GFP and mCherry fluorescence levels obtained 5 hours after induction for 14 TSR constructs. Relative errors for ON and OFF states are from the standard deviation of three biological replicates. ON/OFF GFP fluorescence levels had an average ratio of ~150. ON/OFF mCherry fluorescence levels had an average ratio of ~15.

Flow cytometry histograms of GFP and mCherry fluorescence outputs for TSR hairpin 13 are shown in FIGS. 2A-2B. Measurements were taken 5 hours after the addition of the IPTG. OFF states are displayed on top of the ON states. The GFP fluorescence histograms showed a dynamic range with ON/OFF ratio exceeding 200. The mCherry fluorescence histograms showed a clear difference between the ON and OFF states with a ratio over 30. ON/OFF GFP and mCherry fluorescence levels obtained 5 hours after induction for 14 TSR constructs is shown in FIG. 2C. Nine of the 10 other TSR constructs showed similar performance with one device not activating in response to upstream translation (data not shown). GFP and fluorescence levels had average ON/OFF ratios of ~150 and ~15, respectively. We attribute much of the lower ON/OFF ratio observed for the mCherry output to the relatively low fluorescence of mCherry compared to GFP and higher cell autofluorescence in the mCherry channel. Similar ON/OFF ratios have been observed for toehold switches regulating mCherry.[3] Since OFF states for both GFP and mCherry were very low (FIGS. 2A-2B), the correlation between ON/OFF for GFP and mCherry fluorescence levels is evidence of the correlation between the ON state protein expression levels. Higher GFP expression generally yielded higher mCherry expression level.

Translation-Sensing Riboswitch Inverter (TSRi) Systems

We also designed an inverted TSR system (FIG. 3) in which an active output gene is repressed when the input gene is translated. To our knowledge, no such translational inverter has been demonstrated previously. The TSR inverter (TSRi) also contains a ribosome-sensing hairpin element, however, this element is now upstream of an exposed RBS and start codon that enables translation of the output gene in the absence of upstream translation. The hairpin element in the inverter contains sequences that are complementary to both the RBS and start codon, yet are held in place through strong base pairing within the hairpin. When input gene translation is activated, the ribosome will scan through the mRNA until it encounters a stop codon within the stem of the TSR inverter. During this process, RNA sequences complementary to the RBS and start codon of the output gene are released, the sequences refold to conceal the translation initiation elements, and in turn cause repression of the output gene.

The stem-loop structure of the inverter consists of a 20-nt stem and a 12-nt loop. Arbitrary sequences are indicated in gray (FIG. 3). There is a 2-nt bulge located 10-nt from the bottom of the stem. We designed this bulge to avoid the addition of an RBS at the 5' end of the stem, since we have a reverse complement RBS sequence (RBS*) in the stem near the 3' end. As the ribosome unwinds the inverter hairpin, the reverse complement AUG sequence (AUG*), RBS* and the 6-nt complementary sequence in between will bind to the downstream region ranging from the RBS to the start codon forming a hairpin structure with a 17-nt stem and a 12 nt-loop upstream of the output gene (mCherry). Since these key features for translation initiation are concealed within the hairpin, translation of the output mCherry should no longer occur. It is important to note that there are many different potential TSRi designs that employ different positions of the stop codon, RBS, and start codon to modulate translation of the output gene. These designs can be informed by the mechanisms of riboregulators that repress translation in response to the binding of a trigger RNA.

Use of TSRs to Insulate RNA Sensors from Output Proteins

We also developed a new approach to carry out molecular logic that employs networks of interacting RNAs to evaluate combinations of AND, OR, and NOT logic[6]. These ribocomputing systems make use of arrays of toehold switch sensors that are placed upstream and in frame of a desired output gene in the circuit. We term such RNAs "gate RNAs." Each sensor in the array contains its own RBS and start codon, and each can recognize a cognate trigger RNA to initiate translation of the output gene (FIG. 4A). Since different trigger RNA inputs turn ON gene expression, these gates can function as molecular OR logic gates. Alternatively, riboregulators that repress translation upon trigger RNA binding can be integrated into the array upstream of the output gene. In these repressor systems, gene expression remains ON until all of the upstream riboregulators are deactivated by their cognate trigger RNAs. These gate RNAs can thus function as molecular NAND gates.

Although we have demonstrated that gate RNAs are capable of evaluating up to 6-input OR logic[6], their performance has been limited by the fact that the output gene from the system has different lengths depending on which input RNA was used for activation (FIG. 4A). For instance, the sensor at the 5' end of the gate RNA produces an output protein that can contain over 100 residues encoded by the downstream sensors before the coding sequence of the intended gene is reached. These additional residues can interfere with proper folding of the output protein and prevent it from functioning properly. Thus, a system that insulates the information processing elements of the gate RNA (i.e., the sensor array) from the sequence of the output gene would be highly desirable for enhancing the overall performance and improving the reliability of gate RNAs in ribocomputing devices.

TSRs are very useful tools for accomplishing this insulation function as they can detect activation of a gate RNA and use this stimulus to initiate translation of an unrelated output protein. FIG. 4B demonstrates how a TSR module can be deployed as an insulator within a 6-input OR gate. The TSR is added to the gate RNA downstream of the final sensor module in the transcript. Thus, activation of any of the upstream sensors can cause the ribosome to unwind the TSR and trigger translation of an output gene that lacks any additional N-terminal residues and has the same sequence, no matter which sensor is used to turn ON the system.

To demonstrate this insulator function, we inserted a TSR into a 6-input OR gate RNA used to regulate GFP. Flow cytometry was used to evaluate the GFP expression levels from the circuit in the presence of the six cognate input RNAs and with two non-cognate RNAs that should not interact with the gate RNA. As intended, we found that GFP expression increased by at least 40-fold for all of the cognate input RNAs. Furthermore, variations in expression were negligible for the first four inputs, A through D, which are typically subject to the strongest variations in expression in the absence of the TSR since they encode many additional residues in the output protein. Expression levels are markedly increased in the 3'-most inputs E and F because they do not require the ribosome to translate through as many regions of high secondary structure compared to inputs A through D. This effect is observed in most gate RNAs, in general, including those without TSRs. The TSR-insulated gate RNA also did not exhibit substantial GFP leakage when challenged with a pair of non-cognate RNA inputs G and H.

It is important to note that TSRi systems can also be used to insulate sensor modules from the output protein. When TSRi systems are used in this context, they can also invert the function of the gate RNA transforming an OR gate RNA into a NAND circuit, or transforming a NAND gate RNA into an OR circuit.

Use of TSR Cascades to Amplify Molecular Signals

TSRs also have important applications for amplification of molecular signals detected inside a cell or outside a cell potentially for diagnostic systems. FIG. 5 shows an implementation of a chain of TSR modules incorporated into a single transcript. The transcript begins with a toehold switch module designed to detect an RNA of interest. In the absence of the trigger RNA, all the hairpin modules in the transcript remain intact and translation of any of the reporter genes does not occur. When the trigger RNA is present, the toehold switch hairpin unwinds and translation of the first reporter gene begins. Motion of the ribosome activates the first TSR and initiates translation of the second reporter gene. This cascade reaction continues along the transcript until the Nth TSR is activated to begin translation of its reporter protein.

The net result of this cascade reaction is that a binding of a single trigger RNA activates gene expression from a user-defined number of cistrons within the same transcript. The reporter genes in the mRNA can all be unique and can be used, for instance, to express genes within the same metabolic pathway. Alternatively, all the reporter genes in the mRNA can be identical and thus provide N new active translation sites to amplify production of the reporter. Additional cascade functionalities can be obtained by integrating TSRi systems into the transcript. Such cascades can be used to flip sets of enzymes from one state to another using the signal inversion properties of TSRi modules.

DISCUSSION

Translation sensing riboswitches had a low leakage in response to the trigger activation, although the average ON/OFF mCherry fluorescence level was only 15 due to the relatively weak fluorescence of the mCherry protein itself (FIG. 2C). We are planning on enhancing the ON state by increasing the loop length and/or decreasing the stem length of the riboswitch to increase output gene translation efficiency. Our data also reveal a clear correlation between GFP and mCherry fluorescence levels. Further experiments need to be conducted to understand the effects of different intergenic distances and the upstream gene translation rate on the binding of the ribosome at the downstream RBS whether via ribosome re-initiation or de novo ribosome initiation[4].

In addition, we plan to study systems featuring multicistronic mRNAs featuring multiple TSRs regulating each downstream gene and tandem TSRs that will enable efficient translational coupling between cistrons without affecting the coding sequences of either the input or output genes. Use of multiple TSRs as activators or inverters could enable new forms of genetic feedback in living cells, for instance by using transcription factors or RNA polymerases as output proteins. Furthermore, the translation-sensing riboswitch can serve as a useful reporter tool for investigations of post-transcriptional regulation in prokaryotes and as a means to activate or deactivate entire metabolic pathways in response to a single molecular event.

Lastly, TSRs and TSRi systems have many useful potential applications in diagnostic systems for detection of nucleic acids of interest. The insulation properties of these systems can be used to implement more efficient molecular logic in the diagnostics. OR gates with TSRs, for instance, can detect multiple RNAs associated with a given pathogen or class of pathogens (e.g., methicillin-resistant *S. aureus* markers) and provide improved performance by ensuring the sensor regions do not interfere with the function of the output protein. TSRs and TSRi systems can also be used to provide signal amplification by allowing the binding of a single pathogen RNA to activate reporter translation at multiple sites within a polycistronic mRNA construct. Such signal amplification schemes can improve the sensitivity and speed of diagnostic systems.

MATERIALS AND METHODS

DNA and Bacterial Strains

All DNA oligonucleotides were designed using the NUPACK software package[5] and purchased from Integrated DNA Technologies. *E. coli* strains DH5a (endA1 recA1 gyrA96 thi-1 glnV44 relA1 hsdR17(rκ⁻ mκ⁺) λ⁻) and BL21 Star DE3 (F⁻ompT hsdSB (rB⁻mB⁻) gal dcm rne131 [DE3]; Invitrogen) were used in this study.

Plasmid Construction

Both insert and vector backbone DNA oligonucleotides were amplified via PCR and assembled using Gibson assembly[6] with 30-bp overlap regions. RNA triggers were inserted into pET15b-derived vectors with ampicillin resistance and ColE1 replication origin, whereas the TSR system was inserted into a pCOLADuet-derived vector with kanamycin resistance and ColA replication origin. All plasmids contain a T7 RNA polymerase promoter and terminator pair and a constitutively expressed lacI gene. To ensure all TSRs were synthesized correctly, the assembled constructs were cloned inside DH5α and sequenced.

Growth and Expression Conditions

BL21 Star DE3 *E. coli* cells were used to characterize the systems. Chemically competent cells were transformed with the desired RNA trigger and switch plasmid pair and incubated LB agar plates with appropriate antibiotics: ampicillin (50 ug/ml), kanamycin (30 ug/ml) at 37° C.

For flow cytometry measurements, overnight cultures of cells picked from individual colonies were diluted 100-fold with fresh media shaken at 37° C. for 80 minutes before induction. 0.1 mM isopropyl β-D-1-thiogalactopyranoside (IPTG) were used to induce the T7 RNA polymerase expression which led to the transcription of trigger and switch RNAs. Measurements were taken 3, 4, and 5 hours after induction.

Flow Cytometry Measurements and Analysis

Flow cytometry was performed using a Stratedigm S1000EXi flow cytometer with an A600 HTAS (High Throughput Auto Sampler). Cells were diluted with phosphate buffered saline (PBS) before measurement. Forward scatter (FSC) was used for trigger, and ~40,000 individual cells were analyzed using custom Matlab scripts.

REFERENCES

1. Rex, G., Surin, B., Besse, G., Schneppe, B. and McCarthy, J. (1994). The mechanism of translational coupling in *Escherichia coli*. Higher order structure in the atpHA mRNA acts as a conformational switch regulating the access of de novo initiating ribosomes. *J. Biol. Chem.*, 269, 18118-18127.
2. Oppenheim, D. S. and Yanofsky, C. (1980) Translational coupling during expression of the tryptophan operon of *Escherichia coli*. *Genetics*, 95, 785-795.
3. Green, A. A., Silver, P. A., Collins, J. J. & Yin, P. Toehold switches: de-novo-designed regulators of gene expression. *Cell* 159, 925-939 (2014).
4. Tian, T., & Salis, H. M. (2015). A predictive biophysical model of translational coupling to coordinate and control protein expression in bacterial operons. *Nucleic Acids Research*, 43(14), 7137-7151.
5. Zadeh, J. N., Steenberg, C. D., Bois, J. S., Wolfe, B. R., Pierce, M. B., Khan, A. R., Dirks, R. M., and Pierce, N. A. (2011a). NUPACK: Analysis and design of nucleic acid systems. *J. Comput. Chem.* 32, 170-173.
6. Gibson, D. G., Young, L., Chuang, R.-Y., Venter, J. C., Hutchison, C. A., and Smith, H. O. (2009). Enzymatic assembly of DNA molecules up to several hundred kilobases. *Nat. Methods* 6, 343-345.
7. Green, A. A., Kim, J., Ma, D., Silver, P. A., Collins, J. J., and Yin, P. (2017). Complex cellular logic computation using ribocomputing devices. Unpublished manuscript, currently in revision in *Nature*.

We claim:

1. A synthetic nucleic acid molecule comprising a first nucleotide sequence encoding a first polypeptide, a translation-sensing riboswitch (TSR) configured to adopt a translationally active ON state when the first polypeptide is being translated, and a second nucleotide sequence encoding a second polypeptide, wherein the translation-sensing riboswitch comprises, in order, a stop codon of the first nucleotide sequence, a double-stranded stem-forming domain comprising one or more bulges formed by unpaired nucleotides in said stem-forming domain, and translation initiation elements of the second nucleotide sequence.

2. The synthetic nucleic acid of claim 1, wherein one or both of the first and second nucleotide sequences encodes a fluorescent polypeptide.

3. The synthetic nucleic acid of claim 2, wherein the fluorescent polypeptide is Green Fluorescent Protein (GFP) or mCherry.

4. The synthetic nucleic acid molecule of claim 1, further comprising a toehold switch located upstream of the first nucleotide sequence, wherein the toehold switch comprises a double-stranded stem-forming domain that comprises one or more bulges formed by unpaired nucleotides in said stem-forming domain, a loop-forming domain comprising a ribosomal binding site (RBS), and a sequence complementary to a cognate trigger RNA sequence.

5. A synthetic nucleic acid molecule comprising a first nucleotide sequence encoding a first polypeptide, a translation-sensing riboswitch inverter (TSRi), and a second nucleotide sequence encoding a second polypeptide, wherein the TSRi comprises, in order, a stop codon of the first nucleotide sequence, a double-stranded stem-forming domain comprising one or more bulges formed by unpaired nucleotides in said stem-forming domain, and translation initiation elements of the second nucleotide sequence, and wherein the TSRi is configured to adopt a translationally inactive OFF state when the first polypeptide is being translated.

6. The synthetic nucleic acid molecule of claim 5, wherein one or both of the first and second polypeptides is a fluorescent polypeptide.

7. The synthetic nucleic acid molecule of claim 6, wherein the fluorescent polypeptide is Green Fluorescent Protein (GFP) or mCherry.

8. A method for detecting response of a cell to a stimulus, the method comprising
introducing into a cell the synthetic nucleic acid molecule of claim 4;
detecting an expression level of each of the first and second polypeptides in the cell comprising the introduced synthetic nucleic acid molecule;
exposing the cell comprising the introduced synthetic nucleic acid molecule to a stimulus; and
detecting an expression level of each of the first and second polypeptides in the stimulus-exposed cell, wherein an increase in expression of the second polypeptide following exposure relative to its expression prior to exposure indicates that translation of the first polypeptide was upregulated in the presence of the stimulus, and wherein a decrease in expression of the second polypeptide following exposure relative to its expression prior to exposure indicates that translation of the first polypeptide was downregulated in the presence of the stimulus.

9. The method of claim 8, wherein the first nucleotide sequence encodes a polypeptide endogenous to the cell.

10. The method of claim 8, wherein the second polypeptide is a fluorescent polypeptide.

11. The method of claim 10, wherein the fluorescent polypeptide is Green Fluorescent Protein (GFP) or mCherry.

12. The method of claim 8, wherein the stimulus is a chemical compound.

* * * * *

SEQUENCE LISTING

```
<160> NUMBER OF SEQ ID NOS: 48

<210> SEQ ID NO 1
<211> LENGTH: 140
<212> TYPE: DNA
<213> ORGANISM: Artificial Sequence
<220> FEATURE:
<223> OTHER INFORMATION: synthetic

<400> SEQUENCE: 1
catggcatgg atgaactata caaaaggcct aacactccat cactccacct ccactcccat      60
cccgctctgt tatcggttaa agatagagga gattaaccat gaacagagcg aatttagctg     120
ccgcacagaa aatgcgtaaa                                                 140

<210> SEQ ID NO 2
<211> LENGTH: 48
<212> TYPE: RNA
<213> ORGANISM: Artificial Sequence
<220> FEATURE:
<223> OTHER INFORMATION: synthetic

<400> SEQUENCE: 2
cgcucuguua ucgguuaaag auagaggaga uuaaccauga acagagcg                   48

<210> SEQ ID NO 3
<211> LENGTH: 140
<212> TYPE: DNA
<213> ORGANISM: Artificial Sequence
<220> FEATURE:
<223> OTHER INFORMATION: synthetic

<400> SEQUENCE: 3
catggcatgg atgaactata caaaaggcct aacactccat cactccacct ccactcccat      60
ccgcacgttc tatgtcttaa gaacagagga gattaagaat gagaacgtgc aatttagctg    120
ccgcacagaa aatgcgtaaa                                                 140

<210> SEQ ID NO 4
<211> LENGTH: 48
```

```
<212> TYPE: RNA
<213> ORGANISM: Artificial Sequence
<220> FEATURE:
<223> OTHER INFORMATION: synthetic

<400> SEQUENCE: 4
gcacguucua ugucuuaaga acagaggaga uuaagaauga gaacgugc                    48

<210> SEQ ID NO 5
<211> LENGTH: 139
<212> TYPE: DNA
<213> ORGANISM: Artificial Sequence
<220> FEATURE:
<223> OTHER INFORMATION: synthetic

<400> SEQUENCE: 5
catggcatgg atgaactata caaaaggcct acactccatc actccacctc cactcccatc       60
ccgttcgctt accgttatag aacagaggag atataacatg aagcgaacga atttagctgc      120
cgcacagaaa atgcgtaaa                                                   139

<210> SEQ ID NO 6
<211> LENGTH: 48
<212> TYPE: RNA
<213> ORGANISM: Artificial Sequence
<220> FEATURE:
<223> OTHER INFORMATION: synthetic

<400> SEQUENCE: 6
cguucgcuua ccguuauaga acagaggaga uauaacauga agcgaacg                    48

<210> SEQ ID NO 7
<211> LENGTH: 139
<212> TYPE: DNA
<213> ORGANISM: Artificial Sequence
<220> FEATURE:
<223> OTHER INFORMATION: synthetic

<400> SEQUENCE: 7
catggcatgg atgaactata caaaaggcct acactccatc actccacctc cactcccatc       60
cgcacttgtc acccttatag aacagaggag atataagatg acaagtgca atttagctgc      120 cgcacagaaa atgcgtaaa                                                   139

<210> SEQ ID NO 8
<211> LENGTH: 48
<212> TYPE: RNA
<213> ORGANISM: Artificial Sequence
<220> FEATURE:
<223> OTHER INFORMATION: synthetic

<400> SEQUENCE: 8
gcacuuguca cccuuauaga acagaggaga uauaagaugg acaagugc                    48

<210> SEQ ID NO 9
<211> LENGTH: 140
<212> TYPE: DNA
<213> ORGANISM: Artificial Sequence
<220> FEATURE:
<223> OTHER INFORMATION: synthetic

<400> SEQUENCE: 9
catggcatgg atgaactata caaaaggcct aacactccat cactccacct ccactcccat       60
ccgcactgtc tacctagtta tgatagagga gataactaat gagacagtgc aatttagctg     120
```
ccgcacagaa aatgcgtaaa                                                    140

<210> SEQ ID NO 10
<211> LENGTH: 48
<212> TYPE: RNA
<213> ORGANISM: Artificial Sequence
<220> FEATURE:
<223> OTHER INFORMATION: synthetic

<400> SEQUENCE: 10
gcacugucua ccuaguuaug auagaggaga uaacuaauga gacagugc                      48

<210> SEQ ID NO 11
<211> LENGTH: 140
<212> TYPE: DNA
<213> ORGANISM: Artificial Sequence
<220> FEATURE:
<223> OTHER INFORMATION: synthetic

<400> SEQUENCE: 11
catggcatgg atgaactata caaaaggcct aacactccat cactccacct ccactcccat         60
cccgaatttg catgtagtta caatagagga gataactaat ggcaaattcg aatttagctg        120
ccgcacagaa aatgcgtaaa                                                    140

<210> SEQ ID NO 12
<211> LENGTH: 48
<212> TYPE: RNA
<213> ORGANISM: Artificial Sequence
<220> FEATURE:
<223> OTHER INFORMATION: synthetic

<400> SEQUENCE: 12
cgaauuugca uguaguuaca auagaggaga uaacuaaugg caaauucg                      48

<210> SEQ ID NO 13
<211> LENGTH: 140
<212> TYPE: DNA
<213> ORGANISM: Artificial Sequence
<220> FEATURE:
<223> OTHER INFORMATION: synthetic

<400> SEQUENCE: 13
catggcatgg atgaactata caaaaggcct aacactccat cactccacct ccactcccat         60
cccgctcttg tacctcgtta caatagagga gataacgaat gacaagagcg aatttagctg       120
ccgcacagaa aatgcgtaaa                                                    140

<210> SEQ ID NO 14
<211> LENGTH: 48
<212> TYPE: RNA
<213> ORGANISM: Artificial Sequence
<220> FEATURE:
<223> OTHER INFORMATION: synthetic

<400> SEQUENCE: 14
cgcucuugua ccucguuaca auagaggaga uaacgaauga caagagcg                      48

<210> SEQ ID NO 15
<211> LENGTH: 140
<212> TYPE: DNA
<213> ORGANISM: Artificial Sequence
<220> FEATURE:
<223> OTHER INFORMATION: synthetic

<400> SEQUENCE: 15

```
catggcatgg atgaactata caaaaggcct aacactccat cactccacct ccactcccat    60
ccgttccgtg tgtgctgtta caatagagga gataacagat gacacggaac aatttagctg   120
ccgcacagaa aatgcgtaaa                                               140
```

<210> SEQ ID NO 16
<211> LENGTH: 48
<212> TYPE: RNA
<213> ORGANISM: Artificial Sequence
<220> FEATURE:
<223> OTHER INFORMATION: synthetic

<400> SEQUENCE: 16

```
guuccgugug ugcuguuaca auagaggaga uaacagauga cacggaac                48
```

<210> SEQ ID NO 17
<211> LENGTH: 140
<212> TYPE: DNA
<213> ORGANISM: Artificial Sequence
<220> FEATURE:
<223> OTHER INFORMATION: synthetic

<400> SEQUENCE: 17

```
catggcatgg atgaactata caaaaggcct aacactccat cactccacct ccactcccat    60
ccgtcggtta gatgtcgtta caatagagga gataacgaat gctaaccgac aatttagctg   120
ccgcacagaa aatgcgtaaa                                               140
```

<210> SEQ ID NO 18
<211> LENGTH: 48
<212> TYPE: RNA
<213> ORGANISM: Artificial Sequence
<220> FEATURE:
<223> OTHER INFORMATION: syntehtic

<400> SEQUENCE: 18

```
gucgguuaga ugucguuaca auagaggaga uaacgaaugc uaaccgac                48
```

<210> SEQ ID NO 19
<211> LENGTH: 140
<212> TYPE: DNA
<213> ORGANISM: Artificial Sequence
<220> FEATURE:
<223> OTHER INFORMATION: synthetic

<400> SEQUENCE: 19

```
catggcatgg atgaactata caaaaggcct aacactccat cactccacct ccactcccat    60
cccagtgtta gatcatgtta caatagagga gataacatat gctaacactg aatttagctg   120
ccgcacagaa aatgcgtaaa                                               140
```

<210> SEQ ID NO 20
<211> LENGTH: 48
<212> TYPE: RNA
<213> ORGANISM: Artificial Sequence
<220> FEATURE:
<223> OTHER INFORMATION: synthetic

<400> SEQUENCE: 20

```
caguguuaga ucauguuaca auagaggaga uaacauaugc uaacacug                48
```

<210> SEQ ID NO 21
<211> LENGTH: 139
<212> TYPE: DNA

```
<213> ORGANISM: Artificial Sequence
<220> FEATURE:
<223> OTHER INFORMATION: synthetic

<400> SEQUENCE: 21
catggcatgg atgaactata caaaaggcct acactccatc actccacctc cactcccatc    60
cgcacttatt gcctcgttag aatagaggag ataacgaatg aataagtgca atttagctgc   120
cgcacagaaa atgcgtaaa                                                139

<210> SEQ ID NO 22
<211> LENGTH: 48
<212> TYPE: RNA
<213> ORGANISM: Artificial Sequence
<220> FEATURE:
<223> OTHER INFORMATION: synthetic

<400> SEQUENCE: 22
gcacuuauug ccucguuaga auagaggaga uaacgaauga auaagugc                 48

<210> SEQ ID NO 23
<211> LENGTH: 139
<212> TYPE: DNA
<213> ORGANISM: Artificial Sequence
<220> FEATURE:
<223> OTHER INFORMATION: synthetic

<400> SEQUENCE: 23
catggcatgg atgaactata caaaaggcct acactccatc actccacctc cactcccatc    60
ccgctttatc atggtcttag aacagaggag ataagacatg gataaagcga atttagctgc   120
cgcacagaaa atgcgtaaa                                                139

<210> SEQ ID NO 24
<211> LENGTH: 48
<212> TYPE: RNA
<213> ORGANISM: Artificial Sequence
<220> FEATURE:
<223> OTHER INFORMATION: synthetic

<400> SEQUENCE: 24
cgcuuuauca uggucuuaga acagaggaga uaagacaugg auaaagcg                 48

<210> SEQ ID NO 25
<211> LENGTH: 140
<212> TYPE: DNA
<213> ORGANISM: Artificial Sequence
<220> FEATURE:
<223> OTHER INFORMATION: synthetic

<400> SEQUENCE: 25
catggcatgg atgaactata caaaaggcct aacactccat cactccacct ccactcccat    60
ccgtaatgtg taccgcctta gaacagagga gataaggcat gacacattac aatttagctg   120
ccgcacagaa aatgcgtaaa                                               140

<210> SEQ ID NO 26
<211> LENGTH: 48
<212> TYPE: RNA
<213> ORGANISM: Artificial Sequence
<220> FEATURE:
<223> OTHER INFORMATION: synthetic

<400> SEQUENCE: 26
guaaugugua ccgccuuaga acagaggaga uaaggcauga cacauuac                 48
```

<210> SEQ ID NO 27
<211> LENGTH: 139
<212> TYPE: DNA
<213> ORGANISM: Artificial Sequence
<220> FEATURE:
<223> OTHER INFORMATION: synthetic

<400> SEQUENCE: 27
catggcatgg atgaactata caaaaggcct acactccatc actccacctc cactcccatc       60
cgctaatgtt acctgtatag aacagaggag atatacaatg aacattagca atttagctgc      120
cgcacagaaa atgcgtaaa                                                   139

<210> SEQ ID NO 28
<211> LENGTH: 48
<212> TYPE: RNA
<213> ORGANISM: Artificial Sequence
<220> FEATURE:
<223> OTHER INFORMATION: synthetic

<400> SEQUENCE: 28
gcuaauguua ccuguauaga acagaggaga uauacaauga acauuagc                    48

<210> SEQ ID NO 29
<211> LENGTH: 140
<212> TYPE: DNA
<213> ORGANISM: Artificial Sequence
<220> FEATURE:
<223> OTHER INFORMATION: synthetic

<400> SEQUENCE: 29
catggcatgg atgaactata caaaaggcct aacactccat cactccacct ccactcccat       60
ccgtcgtaag caccgtgtaa gaacagagga gattacacat ggcttacgac aatttagctg      120
ccgcacagaa aatgcgtaaa                                                  140

<210> SEQ ID NO 30
<211> LENGTH: 48
<212> TYPE: RNA
<213> ORGANISM: Artificial Sequence
<220> FEATURE:
<223> OTHER INFORMATION: synthetic

<400> SEQUENCE: 30
gucguaagca ccguguaaga acagaggaga uuacacaugg cuuacgac                    48

<210> SEQ ID NO 31
<211> LENGTH: 139
<212> TYPE: DNA
<213> ORGANISM: Artificial Sequence
<220> FEATURE:
<223> OTHER INFORMATION: synthetic

<400> SEQUENCE: 31
catggcatgg atgaactata caaaaggcct acactccatc actccacctc cactcccatc       60
cgcacgtaat accctgttag aacagaggag ataacagatg attacgtgca atttagctgc      120
cgcacagaaa atgcgtaaa                                                   139

<210> SEQ ID NO 32
<211> LENGTH: 48
<212> TYPE: RNA
<213> ORGANISM: Artificial Sequence
<220> FEATURE:

<223> OTHER INFORMATION: synthetic

<400> SEQUENCE: 32
gcacguaaua cccuguuaga acagaggaga uaacagauga uuacgugc        48

<210> SEQ ID NO 33
<211> LENGTH: 140
<212> TYPE: DNA
<213> ORGANISM: Artificial Sequence
<220> FEATURE:
<223> OTHER INFORMATION: synthetic

<400> SEQUENCE: 33
catggcatgg atgaactata caaaaggcct aacactccat cactccacct ccactcccat     60
ccgcacgtgt aatgctgtta gaatagagga gataacagat gtacacgtgc aatttagctg   120
ccgcacagaa aatgcgtaaa                                                140

<210> SEQ ID NO 34
<211> LENGTH: 48
<212> TYPE: RNA
<213> ORGANISM: Artificial Sequence
<220> FEATURE:
<223> OTHER INFORMATION: synthetic

<400> SEQUENCE: 34
gcacguguaa ugcuguuaga auagaggaga uaacagaugu acacgugc        48

<210> SEQ ID NO 35
<211> LENGTH: 139
<212> TYPE: DNA
<213> ORGANISM: Artificial Sequence
<220> FEATURE:
<223> OTHER INFORMATION: synthetic

<400> SEQUENCE: 35
catggcatgg atgaactata caaaaggcct acactccatc actccacctc cactcccatc     60
ccgcttgtat aggctgttaa gacagaggag ataacagatg atacaagcga atttagctgc   120
cgcacagaaa atgcgtaaa                                                 139

<210> SEQ ID NO 36
<211> LENGTH: 48
<212> TYPE: RNA
<213> ORGANISM: Artificial Sequence
<220> FEATURE:
<223> OTHER INFORMATION: synthetic

<400> SEQUENCE: 36
cgcuuguaua ggcuguuaag acagaggaga uaacagauga uacaagcg        48

<210> SEQ ID NO 37
<211> LENGTH: 140
<212> TYPE: DNA
<213> ORGANISM: Artificial Sequence
<220> FEATURE:
<223> OTHER INFORMATION: synthetic

<400> SEQUENCE: 37
catggcatgg atgaactata caaaaggcct aacactccat cactccacct ccactcccat     60
ccgcacttgt tctaatctta gaacagagga gataagatat gaacaagtgc aatttagctg   120
ccgcacagaa aatgcgtaaa                                                140

```
<210> SEQ ID NO 38
<211> LENGTH: 48
<212> TYPE: RNA
<213> ORGANISM: Artificial Sequence
<220> FEATURE:
<223> OTHER INFORMATION: synthetic

<400> SEQUENCE: 38
gcacuuguuc uaaucuuaga acagaggaga uaagauauga acaagugc         48

<210> SEQ ID NO 39
<211> LENGTH: 139
<212> TYPE: DNA
<213> ORGANISM: Artificial Sequence
<220> FEATURE:
<223> OTHER INFORMATION: synthetic

<400> SEQUENCE: 39
catggcatgg atgaactata caaaaggcct acactccatc actccacctc cactcccatc    60
cgccttgtat actaacttaa gacagaggag ataagttatg atacaaggca atttagctgc   120
cgcacagaaa atgcgtaaa                                                139

<210> SEQ ID NO 40
<211> LENGTH: 48
<212> TYPE: RNA
<213> ORGANISM: Artificial Sequence
<220> FEATURE:
<223> OTHER INFORMATION: synthetic

<400> SEQUENCE: 40
gccuuguaua cuaacuuaag acagaggaga uaaguuauga uacaaggc         48

<210> SEQ ID NO 41
<211> LENGTH: 140
<212> TYPE: DNA
<213> ORGANISM: Artificial Sequence
<220> FEATURE:
<223> OTHER INFORMATION: synthetic

<400> SEQUENCE: 41
catggcatgg atgaactata caaaaggcct aacactccat cactccacct ccactcccat    60
cccgctctgt taccgtaata gaacagagga gatattacat gaacagagcg aatttagctg   120
ccgcacagaa aatgcgtaaa                                               140

<210> SEQ ID NO 42
<211> LENGTH: 48
<212> TYPE: RNA
<213> ORGANISM: Artificial Sequence
<220> FEATURE:
<223> OTHER INFORMATION: synthetic

<400> SEQUENCE: 42
cgcucuguua ccguaauaga acagaggaga uauuacauga acagagcg         48

<210> SEQ ID NO 43
<211> LENGTH: 139
<212> TYPE: DNA
<213> ORGANISM: Artificial Sequence
<220> FEATURE:
<223> OTHER INFORMATION: synthetic

<400> SEQUENCE: 43
catggcatgg atgaactata caaaaggcct acactccatc actccacctc cactcccatc    60
```

```
cgcgtatggt atcggtaaac gacagaggag atttaccatg accatacgca atttagctgc    120
cgcacagaaa atgcgtaaa                                                 139

<210> SEQ ID NO 44
<211> LENGTH: 48
<212> TYPE: RNA
<213> ORGANISM: Artificial Sequence
<220> FEATURE:
<223> OTHER INFORMATION: syntehtic

<400> SEQUENCE: 44
gcguauggua ucgguaaacg acagaggaga uuuaccauga ccauacgc                 48

<210> SEQ ID NO 45
<211> LENGTH: 140
<212> TYPE: DNA
<213> ORGANISM: Artificial Sequence
<220> FEATURE:
<223> OTHER INFORMATION: synthetic

<400> SEQUENCE: 45
catggcatgg atgaactata caaaaggcct aacactccat cactccacct ccactcccat    60
ccgcacttgt tatgtcgtta agatagagga gataacgaat gaacaagtgc aatttagctg   120
ccgcacagaa aatgcgtaaa                                                140

<210> SEQ ID NO 46
<211> LENGTH: 48
<212> TYPE: RNA
<213> ORGANISM: Artificial Sequence
<220> FEATURE:
<223> OTHER INFORMATION: synthetic

<400> SEQUENCE: 46
gcacuuguua ugucguuaag auagaggaga uaacgaauga acaagugc                 48

<210> SEQ ID NO 47
<211> LENGTH: 139
<212> TYPE: DNA
<213> ORGANISM: Artificial Sequence
<220> FEATURE:
<223> OTHER INFORMATION: synthetic

<400> SEQUENCE: 47
catggcatgg atgaactata caaaaggcct acactccatc actccacctc cactcccatc    60
cgttccgcgt gtgctctata agtagaggag aatagagatg acgcggaaca atttagctgc   120
cgcacagaaa atgcgtaaa                                                 139

<210> SEQ ID NO 48
<211> LENGTH: 48
<212> TYPE: RNA
<213> ORGANISM: Artificial Sequence
<220> FEATURE:
<223> OTHER INFORMATION: synthetic

<400> SEQUENCE: 48
guuccgcgug ugcucuauaa guagaggaga auagagauga cgcggaac                 48
```